United States Patent [19]
Kuehne et al.

[11] Patent Number: 5,369,111
[45] Date of Patent: Nov. 29, 1994

[54] MODULATOR AGENT AND USE THEREOF

[75] Inventors: Martin E. Kuehne, Burlington; Linda S. Borman, Essex Junction, both of Vt.

[73] Assignee: University of Vermont, Burlington, Vt.

[21] Appl. No.: 900,745

[22] Filed: Jun. 19, 1992

Related U.S. Application Data

[63] Continuation of Ser. No. 506,615, Apr. 10, 1990, abandoned.

[51] Int. Cl.$^5$ ............................................. A61K 31/44
[52] U.S. Cl. .................................................... 514/283
[58] Field of Search .......................................... 514/283

[56] References Cited

U.S. PATENT DOCUMENTS 4,746,665  5/1988  Szantay ................. 514/283

OTHER PUBLICATIONS

Inaba, M., et al, Non-Antitumor Vinca Alkaloids Reverse Multidrug Resistance in P388 Leukemia Cells in Vitro, Jpn.J.Cancer Res., (Gann), 77, 197–204; Feb. 1986.

Kuehne et al "Three Routes to the Critical C16′–C14 Part relative Stereo–Chemistry of vinblastine . . . " *J. Org. Chem.* 52: 4340–4349 (1987).

Borman & Kuehne "Specific alterations in the biological activities of C–20′–modified vinblastine congeners" *Biochemical Pharmacology* 38(5) 715–724 (Mar. 1, 1989).

"Non–antitumor vinca alkaloids reverse multidrug resistance in P388 Leukemia cells in vitro," Chemical Abstracts CA 104(21):179840q, Inaba, Published 1986.

The Pharmacological Basis of Therapeutics, Goodman and Gilman, Eds., pp. 1284–1285, Publsihed in 1975.

*Primary Examiner*—Frederick E. Waddell
*Assistant Examiner*—Gregory Hook
*Attorney, Agent, or Firm*—Pollock, Vande Sande & Priddy

[57] ABSTRACT

Sensitizing tumoral cells to anticancerous drugs and/or inhibiting the tumoral cells resistance to antitumoral drugs employing as a modulator agent a vinca alkaloid dimer, analog to vinblastine or vincristine, with a low cytotoxicity or devoid of cytotoxicity, comprising at least one stereoisomerism different from that of vinblastine or vincristine in the C-14′, C-16′ or C-20′ position. Notably, the modulator agent may have the R absolute configuration in the C-16′ position.

5 Claims, 17 Drawing Sheets

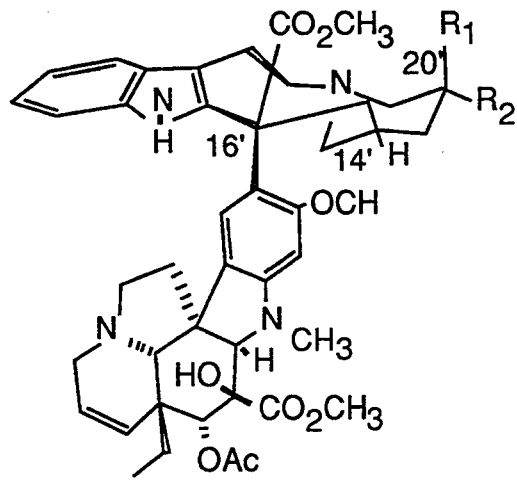
FIG. 1
|  | 16' | 14' | 20' |  |  |
|---|---|---|---|---|---|
| Vinblastine (R₁= OH, R₂= Et) | S | R | S |  |  |
| 14'-Epi-20'-Deethyl 20'- Deoxy-VBL (R₁ = R₂= H) | S | R |  | n° 330 | (PREF) |
| 16'-Epi-20'-Deethyl 20'-Deoxy - VBL | R | S |  | n° 331 | (PREF) |
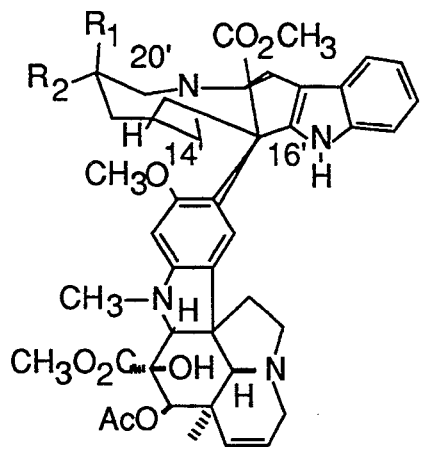
|  | 16' | 14' | 20' |  |  |
|---|---|---|---|---|---|
| Vincovaline (R₁=OH, R₂= Et) | R | S | R |  | (PARF) |
| 20'-Deoxy-Vincovaline (R₁= H, R₂= Et) | R | R | S | n° 336 | (PARF) |
| 20'-Deoxy-14', 16'-Epi-VBL (R₁=Et, R₂= H) | R | R | R | n° 173 | (PARF) |
| 20'- Deoxy-16',20'-Epi-VBL | R | R | S | n° 354 | (PREF) |
| 20'- Deoxy-14'-Epi-VBL | S | S | R | n° 353 | (PREF) |
| 20'-Deoxy-20'-Deethyl-Vincovaline (R₁= R₂= H) | R | R |  | n° 352 | (PARF) |

O ABSENCE OF MODULATOR
△ 1μM, □ 5μM, ▽ 10μM, ο 20μM,
× 50μM OF MODULATOR

MODULATOR AGENT AND USE THEREOF

This is a continuation of application Ser. No. 07/506,615, filed Apr. 10, 1990, now abandoned.

TECHNICAL FIELD

The present invention relates to modulator agents, namely agents which sensitize tumoral cells to antitumoral drugs and agents which stimulate the cytotoxicity of antitumoral drugs in tumor cells resistance to antitumoral drugs and use thereof. Such drug resistance can be of an intrinsic nature or acquired through previous drug exposure.

The present invention also relates to a kit of parts for simultaneous, separate or sequential use in anticancerous therapy containing a modulator agent according to the present invention and an antitumoral drug.

BACKGROUND ART

The development of primary drug resistance and the associated phenomenon of multidrug resistance (MDR) in relapsed cancer (1), are major determinants of treatment failure. The therapeutic means to circumvention of MDR is under intensive experimental study using a variety of tumor cell systems that express the phenotype. It is known that MDR cells accumulate less drug than parental, sensitive tumor cells due to the enhanced expression of an efflux pump, termed P-glycoprotein (see reviews 2,3). Compounds have been identified which can sensitize MDR cells to anticancer drugs in combination treatments (4–8). These modulators of drug resistance, typically weak cytotoxic agents without antitumor activity by themselves, enhance the intracellular drug concentration.

The first identified modulators of MDR in cultured cells were the calcium channel blocker verapamil (19) and the calmodulin inhibitor trifluorperazine (20). Since then, numerous other diverse compounds, such as reserpine (5), non-antitumor monomeric vinca alkaloids (14) and ADM analogs (13) have been shown to sensitize MDR cells to the anticancer drugs of the phenotype.

Generally, the known modulators sensitize MDR cells to all of the drugs in the resistance profile, with less pronounced or nonexistent effects on parental cells.

SUMMARY OF INVENTION

It is an object of the present invention to provide new drug resistance modulator agents and use thereof.

It is another object of the present invention that the agents can be easily prepared synthetically.

It is another object of the present invention to provide modulator agents, the modulation of which could be drug and/or cell type selective.

To do this, the present invention provides modulator agents sensitizing tumoral cells to anticancerous action and/or inhibiting the intrinsic or acquired resistance of tumoral cells to said drugs characterized in that it consists in a binary vinca alkaloid, analogous to vinblastine or vincristine, possessing at least one stereoisomerism in the C-16', C-14' or C-20' position which is different from that of the vinblastine or vincristine ones.

In the present patent application, the word "stereoisomerism (or "epimer"hereafter "epi") means an orientation change in space of radials or atoms fixed in these positions.

The S absolute configuration in the C-16' position is essential for the antitumoral activity of the vinblastine or vincristine analogs. Now, preferably, the compounds according to the invention should have low activity or be devoid of activity per se as cytotoxic agents.

This is the reason why among the compounds according to the invention of special interest are those which preferably have at least one stereoisomerism which differs from that of vinblastine or vincristine in the C-16' position, namely an R absolute configuration in C-16', the absolute configurations in C-14' or C-20' being R or S.

In one embodiment of the compounds according to the invention, they differ from vinblastine or vincristine at least by a different stereoisomerism in the C-16' and-/or C-14' positions.

The modulator agents, analogs of vinblastine or vincristine according to the invention, may further differ from vinblastine or vincristine with respect to the nature of the substituents in the C-20' position.

A stereoisomerism change in C-16' involves a different absolute configuration descriptor (R vs. S) for this position. This is not necessarily the case for a change in the C-14' or C-20' stereoisomerism because the absolute configuration descriptors (R vs. S) of the C-14' or C-20' position are dependent on the substituent nature in C-20'.

Anyway, the compounds according to the invention shall have necessarily:
  either at least a different absolute configuration than vinblastine or vincristine in C-14' and/or C-16',
  or a PREF relative configuration in C-14'-C-16' which differs from the PARF vinblastine and vincristine relative configuration in C-14'-C-16'.

The PREF or PARF relative configuration terminology has been defined interalia in F. A. Carey and M. E. Kuehne, Journal Org. Chem., 1982, 47, 3811.

BEST AND VARIOUS MODES FOR CARRYING OUT INVENTION

In a particular embodiment of the compounds according to the present invention, the compounds have the following formula I:

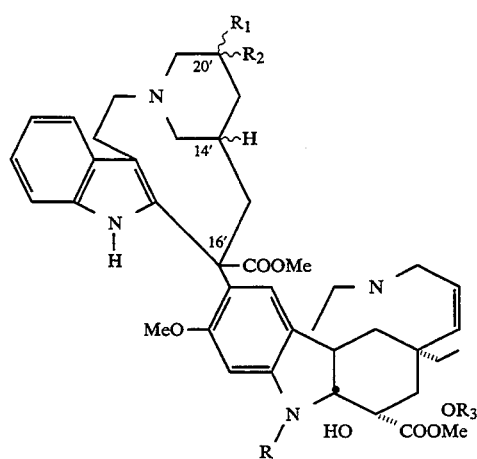

wherein
R = formyl or methyl
$R_1$ = H, OH, or $C_1$–$C_7$ alkyl
$R_2$ = H, OH, or $C_1$–$C_7$ alkyl
$R_3$ = H or acetyl.

The chemical synthesis of the formula I compound according to the invention was disclosed in EP 292 463 and in Kuehne J. Org. Chem. 52, 4340–4349, 1987 (11) and J. Org. Chem., 1989, 54, 3407–3420 (12).

Otherwise, the compounds according to the invention can be prepared according to the process known to a man skilled in the art such as those of Potier J. Am. Chem. 50, 98, 7017 (1976) and (27, 28, 29, 30), Kutney Helv. Chim. Acta. 59, 2858 (1976) and (31, 32, 33, 34, 35) and Schill (36, 37, 38).

These processes yield a mixture of diastereoisomers. It is then sufficient to isolate the diastereoisomer of the invention.

In summary, the synthesis of compounds of formula I can be carried out briefly hereafter exposed in reference to schemes Ia and Ib.

The E - enamino acrylates 125 are obtained by condensation of azepinoindole 153 and appropriate aldehydes 154 and by benzylation of the resulting methanoazepinoindole derivatives 155.

The intramolecular reactions of these seco-secodines 125 involve the formation of tetracyclic compounds 152.

The chlorination of vinylog urethane 152a (A=tosyl) by terbutyl hypochlorite, followed by a reaction at room temperature or a lower temperature with silver tetrafluoroborate and with protonated vindoline allows the quasi exclusive formation of the compounds 157, 158 with the relative stereoisomerism C-16'/C-14' S/R or R/S (parf) (39).

The reaction of the imine-indoline compounds 158 with potassium borohydride in acetic acid involves a break of the C-3'-C-7' bond and the reduction of the resulting imonium function.

The final step of the synthesis consists in a cyclisation reaction of derivatives 163a (A=tosyl) by heating, followed with a debenzylation by catalytic hydrogenation of resulting quaternary salts and subsequent heating of the debenzylation product for conformational adjustment.

Scheme Ia

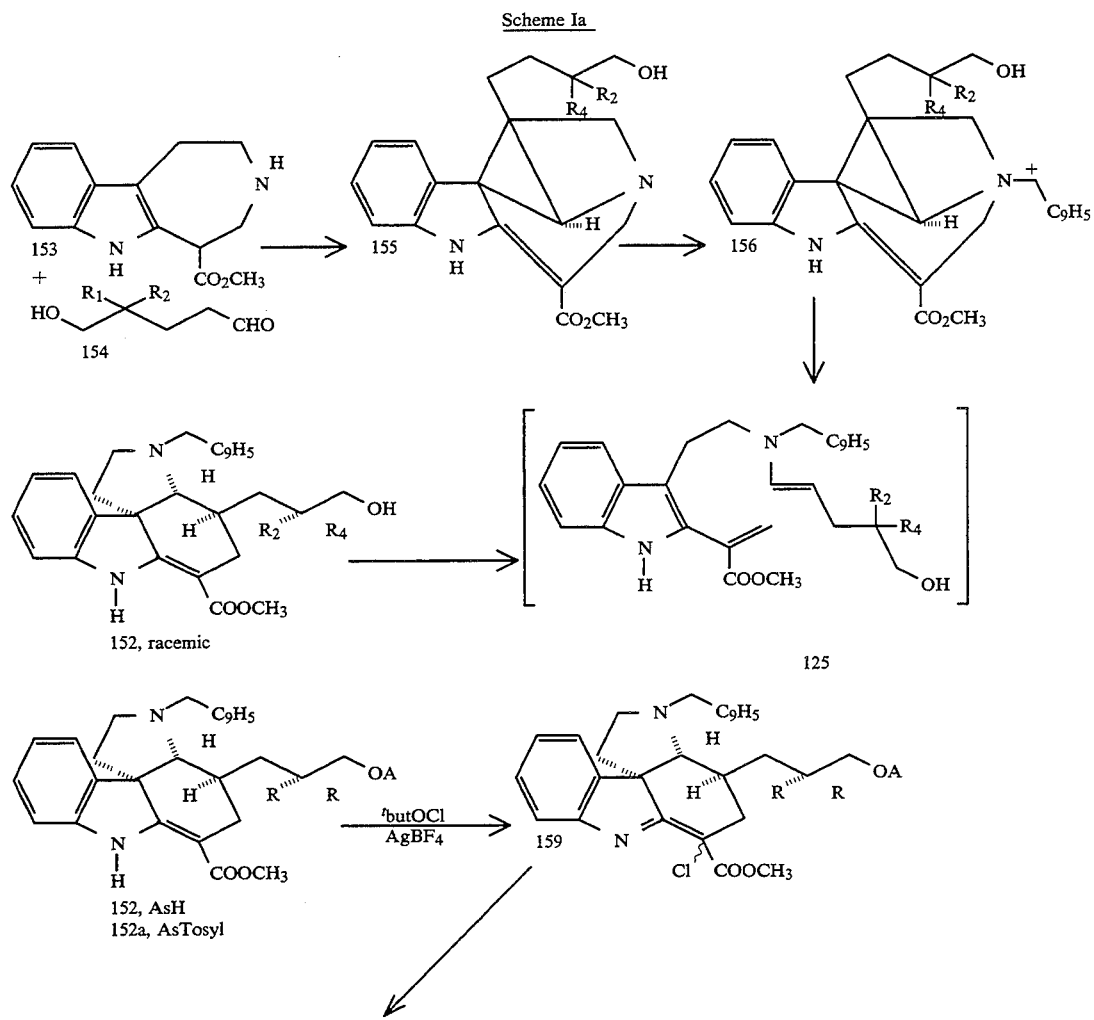

-continued
Scheme Ia

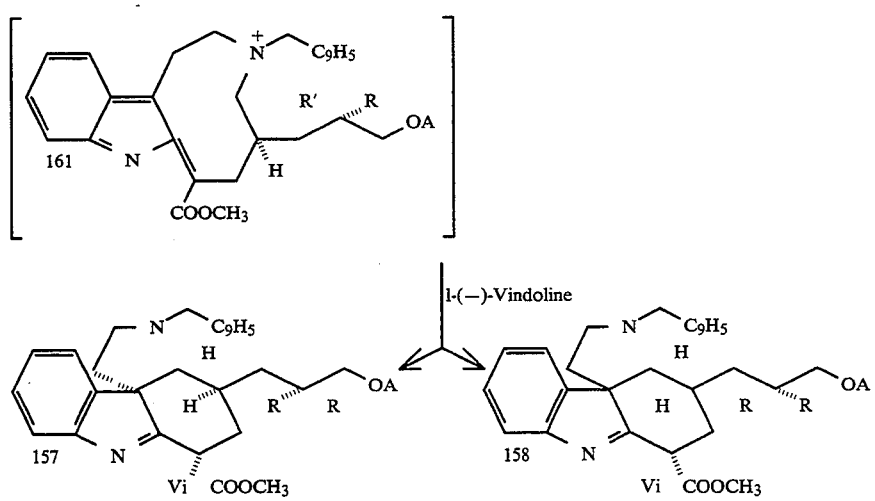

Scheme Ib

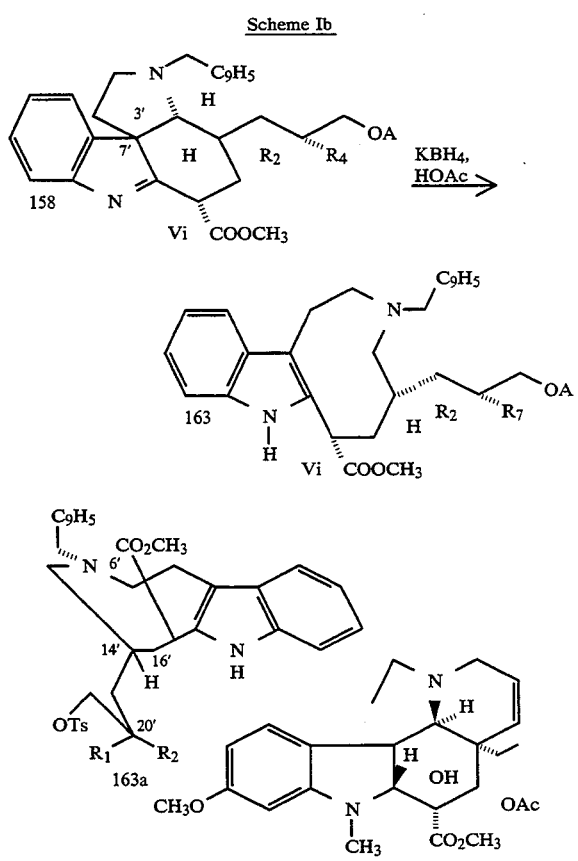

-continued
Scheme Ib

Among the modulator agents according to the invention, may be mentioned vincovaline, which is a natural diastereoisomer (epimeric at C-14′, C-16′ and C-20′) of vinblastine. This compound, like the preferred compounds according to the invention, has low activity or is devoid of activity as a cytotoxic agent.

The doses of the compounds according to the invention required for resensitizing cells with acquired resistance to the anticancerous drugs are proportioned to the level of resistance to each drug. The compounds according to the invention are used as modulator agents within the nontoxic concentration limit, that is to say within an acceptable concentration regarding toxicity. Such amounts can be readily determined by persons skilled in this art upon being made aware of the present application without undue experimentation.

The modulator agents according to the invention enhance interalia the cytotoxic activity of anticancerous drugs such as anthracyclines, vinca alkaloids, epipodophylotoxines and their antitumorous derivatives, this listing being not limitative.

As modulator agents according to the invention of special interest are the compounds which have the R absolute configuration in C-16′ and substituents in C-20', which are different than those in vinblastine and vincristine, especially the compounds of formula I wherein ($R_1$, $R_2$) is different than (OH, ethyl). This change in C-20' involves an enhancement of the modulation.

The modulator agents which are vinblastine analogs according to the invention, namely for which $R=CH_3$ and $R_3=$acetyl modulate advantageously the cytotoxic activity of anticancerous drugs in parental tumor cells (intrinsic resistance) with evidence of drug-selectively.

This modulation is particularly important for the compounds wherein $R=CH_3$ $R_3=$acetyl and ($R_1$, $R_2$)=(H,ethyl) (H,H) (H,Met) or (Met, Met) in the C-20' position.

Notable are the C-20' deoxyvincovaline ($R_1=H$, $R_2=Et$) with an S absolute configuration in C-20' (compound n° 336), the C-20'-deoxydeethylvincovaline ($R_1=H$, $R_2=H$) with the R absolute configuration in C-14' (compound n°352) and the C-16' epi-C-20'-deoxy-C-20'-deethylvinblastine with S absolute configuration in C-14' (compound n° 331), and the C-20'-dimethyl, C-20'-deoxy-deethyl-vincovaline with R configuration in C-14' (compound n° 355) and C-20'-deoxy-C-16', 20' epi VBL (compound n° 354).

The latter modulator agents, analogs of vinblastine, act selectively, that is to say they enhance, preferentially, the cytotoxic activity of drugs other than vinblastine, such as adriamycine (ADM) (which is also called doxorubicine (DOX)), and/or vincristine (VCR) and their antitumorous derivatives in turmoral cells of intrinsic resistance.

Other modulator agent analogs of vinblastine which can be cited according to the invention are the C-14'-epi-C-20'-deethyl C-20'-deoxy-vinblastine (compound n° 330) and C-14'-epi-C-20'-deoxy-VBL (353), which have the PREF C-14'-C-16' relative configuration.

The present invention further provides a kit of parts containing combined preparation for simultaneous, separate or sequential use in cancerous therapy, combining a modulator agent according to the invention and an anticancerous drug.

The modulator agents according to the invention are of particular interest when they are combined with anticancerous drug derivatives which display an enhanced selectivity towards tumoral cells and/or a reduced toxicity. There, notably, are conjugate compounds formed between drug and targeting agents. There, also to be noted, are low toxicity derivative such as N-leucyl doxorubicine. There should be further noted vinca alkaloid derivatives comprising a $C_7$–$C_{20}$ O-acyl group in the C-3 or C-4 position and/or one of several amino-acids as O-acyl substituents in C-3 or C-4 position together with their conjugates with carrier protein.

MATERIALS AND METHODS

Cell culture

The analogs were examined in a panel of tumor cell lines of both intrinsic and acquired drug resistance, as described in Table 1. The rat colon adenocarcinoma cell lines RCC-2 and RCC-5 (ref. 13) were maintained in Ham's F12 medium supplemented with 5% heat-inactivated, fetal bovine serum (Sterile Systems. Hyclone, Logan, Utah). The two rat colon cancer cell lines differ in their degree of cellular differentiation; whereas the RCC-2 cell line is undifferentiated, the RCC-5 cell line is highly mucinous. The human epidermoid carcinoma cell line KB-3-1 and its MDR variant KB-V1, selected by VBL treatment (ref. 14; courtesy of M. Gottesman. National Cancer Institute), was maintained in DMEM medium supplemented with 10%, heat-inactivated, fetal bovine serum. The murine sarcoma cell line SISO and its MDR strains A3 and A10 selected by ADM treatment (ref. 15; courtesy of T. Tritton, Dept. Pharmacology, Univ. Vermont). were maintained in DMEM medium supplemented with 10% heat-inactivated, horse serum (Hazelton Biolog. Lenexa, Kans.). Stock cultures were subcultured twice weekly upon reaching the late exponential phase of population growth: population doubling times were 18–24 h. Antibiotics were not used in stock or experimental cultures. The MDR cell strains were grown in drug-free media for 48 h prior to experimental use.

Mid-exponential cultures were used for all assays. The RCC-2 and RCC-5 cell lines were seeded into 24-well plates at $2 \times 10^4$ cells/well and allowed to attach to the substratum for 16–18 h prior to treatment. The S180 cell lines were seeded into culture tubes at $1 \times 10^5$ cells/ml and treated immediately. Cytotoxicity was determined by quantitation of population growth after 72 h incubation by electronic particle counter (Coulter Electronics, Hialeah, Fla.). The human tumor cell lines were used in a clonogenic assay for cytotoxicity. Cells were seeded at 300 cells/dish, incubated overnight and then treated. Colonies were scored 7–11 days later. In all assays of analog modulation of drug sensitivity, the analog was added minutes prior to the addition of cytotoxic drug.

TABLE I

CELL CULTURE SYSTEMS

| | $IC_{50}$ (μM) | | |
|---|---|---|---|
| | VBL | VCR | ADM |
| I. Intrinsic Drug Resistance | | | |
| A. Rat colon adenocarcinoma cell lines: | | | |
| RCC-2 | 0.003 | 0.005 | 0.01 |
| RCC-5 | 0.008 | 0.015 | 0.05 |
| II. MDR cell systems | | | |
| A. Mouse sarcoma S180, parental | 0.008 | 0.03 | 0.1 |
| B. Human epidermoid carcinoma KB-3-1, parental | 0.001 | 0.002 | 0.015 |

| and their relative MDR cell strains | Relative resistance* | | |
|---|---|---|---|
| | VBL | VCR | ADM |
| A1. S180/A3 | 3 | 7 | 15 |
| A2. S180/A10 | 15 | 17 | 90 |
| A3. KB-V1 | 200 | 400 | 500 |

*calculated by dividing the $IC_{50}$ of each drug in the MDR cell line by the $IC_{50}$ of the parental cell line.

CHEMICALS

C-14', 16', 20'-epi-VBL (vincovaline), C-20'-deoxy C-14', 16', 20'-epi-VBL. C-20'-deoxy-20'-deethyl-C-14', 16'-epi-VBL and the corresponding compounds which are epimeric only at C-14' or at C-16' were synthesized in our laboratory as the free bases, using recently developed protocols (11.112). Vindoline, free base, was obtaine from Omnichem, Louvain-La-Neuve, Belgium. All compounds were dissolved in dimethylsulfoxide at a concentration of 0.01M just prior to use. We purchased VCR sulfate solution. VBL sulfate and ADM HCl from Adri Labs., Columbus, Ohio. The latter two drugs were used from fresh stock solutions in 0.9% saline or ethanol, respectively.

RESULTS

EXAMPLE 1: Vincovaline and C-20'-deoxy-vincovaline

A new synthetic vinblastine (VBL) analog, C-20'-deoxy C-14', 16', 20'-epi-VBL, was examined for its ability to modulate drug resistance in a murine sarcoma S180 cell system, consisting of a parental cell line and two multidrug resistant (MDR) cell strains, A3 and A10, of increasing resistance levels. The profile of activity of the analog was compared to that of vindoline, the lower moiety of VBL, which is a known modulator of MDR in several cell systems. Also, we examined C-14', 16', 20'-epi-VBL, which is a natural product (vincovaline) but which was synthesized for this work. The S180 cell system showed cross-resistance to each of the binary compounds. Overall, the two compounds were poor inhibitors of cell growth with $IC_{50}$ values $>10^{-5}M$. In contrast, the monomer vindoline was equitoxic to parental and MDR cell lines, with an IC50 of $4 \times 10^{-5}M$. When the parental S180 cell line was treated with a combination of our analog and each of several drugs of the MDR phenotype, there occured a modulation of sensitivity that was drug-selective. The C-20'-deoxy Vincovaline elicited a similar, concentration-dependent enhancement of vincristine (VCR) and adriamycin (ADM)-cytotoxicity, but it had no effect on VBL toxicity, over of 50-fold concentration range. In contrast, both vindoline and synthetic vincovaline sensitized the parental S180 cells to all three drugs. Our analog was a superior modulator of VCR and ADM cytotoxicity in parental cells, based on potency. The MDR cell strains, A3 and A10 were examined, similarly. Here, all compounds, the two diastereoisomers and vindoline, were modulators of cellular resistance to VBL, VCR and ADM. We determined the concentration of each modulator required for complete reversal of drug resistance among the MDR cell strains. Whereas, a narrow threshold concentration of vindoline $(0.7 - 1.1 \times 10^{-5}M)$ restored parental sensitivity in MDR cells displaying a 3- to 20-fold range in resistance levels, the reversing concentration of each diastereoisomer was proportioned to the level of resistance to each drug. These results suggest that the binary vinca alkaloids may be competitive inhibitors of drug efflux. We report the first example of a modulator of MDR with significant and drug-selective activity in parental cells.

A. Inherent cytotoxicity

A3 and A10 are two MDR cell strains, of increasing levels of resistance (Table II) that were derived from the S180 cell line by ADM treatment (15). We examined three vinca alkaloids in this system: vindoline, which is the lower moiety of VBL, and two binary, VBL-type diastereoisomers. C-20'-deoxy C-14', C-16', C-20'-epi-VBL and C-14', 16', 20'-epi-VBL (see FIG. 1). The latter compounds were synthetic. Whereas the VBL diastereoisomer (vincovaline) is a natural product, the C-20'-deoxy derivative is a new VBL congener.

TABLE II

| | IC50 ($\times 10^{-8}M$) | | |
|---|---|---|---|
| | VBL | VCR | ADM |
| THE S180 CELL SYSTEM | | | |
| S180, parental | 0.8 | 3.0 | 10.0 |
| RELATIVE RESISTANCE* | | | |
| A3 | 3 | 10 | 15 |

TABLE II-continued

| | IC50 ($\times 10^{-8}M$) | | |
|---|---|---|---|
| | VBL | VCR | ADM |
| A10 | 15 | 20 | 90 |

*calculated by dividing the IC50 of each drug in the resistance cell line by the IC50 of the sensitive, parental cell line.

The toxicity of these compounds to the S180 cell system is shown in FIG. 2. Whereas vindoline inhibited the growth of the parental and MDR cell strains with a similar dependence on concentration, each of the diastereoisomers displayed a resistance profile in the S180 cell system. The C-20'-deoxy Vincovaline was a very weak cytotoxic agent whose non-toxic concentration limit was beyond the limits of solubility.

Modulation of Intrinsic Drug Resistance

The ability of the compounds to modulate drug sensitivity in parental cells was studied over a range of concentrations of each compound, from $10^{-6}M$ to the non-toxic ($IC_{10-20}$) or solubility limit. The effect of C-20'-deoxy vincovaline on the dose-response curve of S180 cells to ADM is presented in FIG. 3. We observed a progressive sensitization of the cells to the drug with increasing analog concentrations. From such experiments, we determined a sensitivity index derived from the IC50 of the drug without modulator treatment divided by the drug IC50 at each concentration of modulator.

When the sensitivity index for each drug, VBL, VCR and ADM is plotted versus the modulator concentration (FIG. 4), we can compare the relative potencies of the compounds as modulators of drug toxicity to the parental S180 cells. We found that our analog, C-20'-deoxy vincovaline, elicited a similar, concentration-dependent enhancement of VCR and ADM cytotoxicity in S180 cells, but that it had no effect on cell sensitivity to VBL, over a 50-fold concentration range. Vincovaline was a weak modulator of drug sensitivity in the parental cell line. The vinca alkaloid monomer, vindoline, sensitized S180 cells to all three drugs with a similar dependence on its concentration. Of the three vinca alkaloid modulators examined, C-29'-deoxy vincovaline is the most potent modulator of intrinsic resistance to ADM and VCR in the S180 cell line.

C. Modulation of acquired drug resistance in MDR cells

To evaluate the ability of vindoline and the two diastereoisomeric VBL analogs to modulate the MDR phenotype (acquired resistance) of the A3 and A10 cell stains, we determined the concentration of compound required to restore drug sensitivities to parental levels. This was done by exposing the MDR cell line to a concentration range of modulator in the presence VBL, VCR and ADM at the respective IC70s of the parental cell line. The cytotoxicity curves for A3 and A10 cells, shown in FIG. 5, are distinctive among the three vinca alkaloids examined. In each cell line, there was a minimum concentration of modulator that elicited 70% growth inhibition for each drug - i.e. the reversing concentration.

We plotted this reversing concentration of modulator versus the drug resistance levels for each drug in the MDR cell strains (FIG. 6). For both VBL-type diastereoisomers, the amount of compound required to restore parental sensitivities to each drug was proportional to the degree of resistance to that drug. This correllation was not observed for the monomer, vindoline.

Another noteworthy observation to be made from FIG. 6, is that our analog. C-20'-deoxy vincovaline, is a modulator capable or reversing completely the high level ADM resistance (90 fold) of A10 cells. Both vindoline and the vincovaline, especially, were limited in this activity by their own cytoxicity in the MDR cell lines.

Our compound. C-20'-deoxy vincovaline, is a strong enhancer of drug toxicity in a parental cell line. This action is drug-selective, since the compound sensitizes S180 cells to ADM and VCR but not to VBL. The compound reverses MDR in the A3 and A10 cell strains, without evidence of drug-specificity. Therefore, the action of this modulator is distinctive among tumor cells based on the nature of their drug resistance-intrinsic (wild-type) or acquired (MDR). Vincovaline is a poor modulator of drug sensitivity in the parental cell line, and significant activity with MDR cells is coincident with its non-toxic concentration limit in each cell line. Therefore C-20' modification of the VBL diastereoisomer results in marked improvement in modulator potency and the acquisition of selectivity of action. Vindoline exhibited no evidence of selective modulation as expected of a typical MDR modulator.

FIG. 7A displays the cytotoxicity of C-20'-deoxy vincovaline in the rat colon adenocarcinoma cell lines RCC-2 and RCC-5. The analog elicited a modest sensitization (2- to 4-fold) of the cell lines to VBL, VCR and ADM at the non-toxic concentration limit of 1-2 $\mu$M.

EXAMPLE 2: C-20'-deoxy-deethyl vincovaline

A. Inherent cytotoxicity

C-20'-deoxy deethyl vincovaline (FIG. 1), henceforth denoted as analog n° 352, was weakly cytotoxic in all of the cell lines described in Table 1, with $IC_{50}$ values of $\leqq 20$ $\mu$M. FIG. 7B depicts the population growth inhibition of analog n° 352 in the rat colon cancer cell lines. RCC-2 and RCC-5. The absence of the $R^2$-ethyl group in analog n° 352 resulted in a 10-fold reduction in cytotoxicity to the colon cancer cell lines, compared to our analog C-20'-deoxy vincovaline (see Panel A).

B. Modulation of Intrinsic drug resistance

FIG. 8 depicts the enhancement of ADM cytotoxicity in parental S180 cells that was dependent on the concentration of C-20'-deoxy deethyl vincovaline. Similar results were obtained in modulation experiments with vinblastine (VBL) and vincristine (VCR), although the maximum degree of sensitization to the latter drugs (2.3–2.7-fold) was lower than that observed for ADM toxicity (5.5-fold) in the presence of the analog. The modulation of VCR sensitivity by analog n° 352 in the rat colon cancer cell lines RCC-2 and RCC-5 is shown in FIG. 9. The analog at 10–20 $\mu$M was able to overcome the greater intrinsic resistance of the RCC-5 cell line to VCR, compared to RCC-2. The very weak cytotoxicity of analog n° 352 in the RCC-5 cell line permitted a maximum sensitization to VCR of 28-fold.

FIG. 10 presents a summary of the potencies of C-20'-deoxy deethyl vincovaline as a modulator of drug sensitivity in the parental cell lines. We have included results with the human epidermoid carcinoma cell line KB-3-1, which was sensitized 3–5 fold to all three drugs by analog n° 352.

C. Modulation of acquired resistance in MDR cells

In the S180/MDR cell system (FIG. 11), C-20'-deoxy deethyl vincovaline restored complete parental sensitivity to VBL, VCR and ADM in cells exhibiting low to moderate resistance levels (3–17-fold) and achieved 80% reversal of high level ADM resistance (90-fold. A10 cell line). The MDR cell strain of the human KB cell line. KB-VI (FIG. 10), which is highly resistant to ADM, VBL and VCR ($\geqq 200$-fold) was sensitized 6-fold to VCR only, at the non-toxic concentration limit of 20 $\mu$M of analog n° 352.

In summary, the analog n° 352 has many favorable properties for a modulator of the cytotoxicity of anticancer drugs. The compound is a very weak cytotoxic agent alone, it can reverse high level (90-fold) ADM resistance in MDR cells, and its activity in parental (intrinsically resistant) cell lines shows evidence of drug- and cell type- selectively. These attributes are not shared by the known MDR modulator vindoline, the lower moiety of VBL, but are held in common with another analog which we have synthesized, C-20'-deoxy vincovaline, which was described in example 1.

EXAMPLE 3: Biological evaluation of additional epimers of C-20' modified vinblastine analogs: the C-14' and C-16' epimers of C-20'-deoxy vinblastine and C-20'-deoxy deethyl vinblastine as modulators of cellular-drug resistance The C-14' and C-16' epimers of C-20'-deoxy VBL (analogs n° 353 and n° 354, respectively) and of C-20'-deoxy deethyl VBL (analogs n° 330 and n° 331, respectively) are weakly cytotoxic in the S180/MDR cell system and the rat colon cancer cell lines, with IC50 values of $\geqq 5$ $\mu$M. Each of the analogs modulated intrinsic cellular resistance to ADM and/or VCR, but had less effect on the sensitivity of parental cells to VBL (Table III). Notable is the large (7–18-fold) enhancement of VCR cytotoxicity achieved in the parental cell lines by the C-14' and C-16' epimers of C-20'-deoxy VBL.

The potency of each analog as a reversal agent for MDR in the S180 cell system is presented in Table IV. The C-14' and C-16' epimers of C-20'-deoxy VBL restored parental sensitivity to all drugs (VBL, VCR and ADM) over a range of 3–90-fold resistance (80% reversal in the case of high level ADM resistance). Potencies are similar between the two epimers of C-20'-deoxy VBL. The activity of the C-14' and C-16' epimers of C-20'-deoxy deethyl VBL in MDR cells was less favorable; full restoration of parental drug sensitivity was achieved for VBL and low level VCR resistance, only.

In summary, the C-14' and C-16' epimers of C-20'-deoxy VBL and C-20'-deoxy deethyl VBL are weak cytotoxic agents. They exhibit drug-selective sensitization of parental cells and modulate the MDR phenotype with a potency that is dependent on the resistance level of the MDR cell strains. The C-14' and C-16' epimers of C-20'-deoxy VBL are superior to those of C-20'-deoxy deethyl VBL as modulators of MDR.

TABLE III

MAXIMUM SENSITIZATION OF PARENTAL CELLS BY MODULATOR*

| CONGENER | CELL LINE | DRUG ADM | VBL | VCR | MODULATOR CONCEN- TRATION |
|---|---|---|---|---|---|
| A. C-20'-deoxy VBL: | | | | | |
| epi-C-14' | S180 | 4.0 | 1.4 | 7.0 | 40. |
|  | RCC-2 | 2.1 | 1.8 | 7.3 | 10. |
|  | RCC-5 | 6.4 | 1.6 | 3.5 | 10. |
| epi-C-16' | S180 | 5.0 | 1.0 | 3.0 | 20. |
|  | RCC-2 | 1.9 | 1.2 | 4.0 | 5. |
|  | RCC-5 | 5.3 | 1.9 | 18.0 | 5. |

TABLE III-continued
MAXIMUM SENSITIZATION OF PARENTAL CELLS BY MODULATOR*

| CONGENER | CELL LINE | DRUG ADM | VBL | VCR | MODULATOR CONCEN- TRATION |
|---|---|---|---|---|---|
| B. C-20'-deoxy deethyl VBL: | | | | | |
| epi-C-14' | S180 | 4.2 | 1.0 | 2.0 | 20. |
|  | RCC-2 | 1.0 | 1.0 | 2.0 | 10 |
|  | RCC-5 | 2.2 | 2.0 | 6.0 | 10 |
| epi-C-16' | S180 | 3.4 | 1.0 | 2.5 | 50. |
|  | RCC-2 | 1.0 | 1.0 | 2.0 | 10. |
|  | RCC-5 | 3.5 | 1.0 | 2.0 | 20. |

*calculated as the $IC_{50}$ of the drug alone divided by the $IC_{50}$ of the [drug - modulator] combination. Data are presented from tretments with the non-toxic concentration limit of each analog as noted.

TABLE IV
MODULATOR POTENCY IN MDR CELLS* ($\mu M$)

| | Drug Resistance Level | | | | | |
|---|---|---|---|---|---|---|
| | ADM | | VBL | | VCR | |
| CONGENER | 15 | 90 | 3 | 10 | 7 | 17 |
| C-20'-deoxy VBL: | | | | | | |
| epi-C-14' | 35. | 40.# | 4.0 | 10.0 | 4.0 | 13.0 |
| epi-C-16' | 25. | 40. | 1.7 | 10.0 | 10.0 | 20.0 |
| C-20'-deoxy deethyl VBL: | | | | | | |
| epi-C-14' | >NT | no effect | 5.2 | 18. | 11. | >NT |
| epi-C-16' | >NT | no effect | 5.0 | 34. | 10. | >NT |

*The minimal concentration of modulator required to restore the drug sensitivity of S180/MDR cell strains to that of parental S180 cells. Data are the averages of 2-3 separate experiments, S.D. ≦20%.
Significant (>50%) reversal of drug resistance at the maximum non-toxic concentration of modulator.
>NT Partial (<50%) reversal of drug resistance at the maximum non-toxic concentration limit of modulator.

EXAMPLE 4: Modulation by C-20'-deoxy C-20'-deethyl vincovaline of resistance P388 cell lines

A. CELLULAR LINES

The sensitization of C-20'-deoxy C-20'-deethyl vincovaline (D-DEV) has been tested on sensitive and resistants $P_{388}$ cell lines originating from mouse lympnoma.

The resistance to anticancerous drug has been induced on $DBA_2$ mouses bearing $P_{388}$ cells ascites and maintained by treatment with adryamycin.

This $P_{388}$ R line also displays a resistance to vinca alkaloids.

B. CYTOTOXICITY OF ANTITUMOROUS DERIVATIVES IN RESPECT TO $P_{388}S$ AND $P_{388}$ $DOX_R$ LINES

The $P_{388}S$ and $P_{388}R$ cells (10 TO 15000 cells per well) are incubated at 37° C. with increasing quantities of adryamycin (ADM, vinblastine (VBL) and vincristine (VCR). The concentrations used for these experiments together with the cytotoxicity results are apparent in figures 12 to 14. These figures show the resistance of $P_{388}$ R cells to cytotoxic activity of the antitumoral drugs (ADM. VBL and VCR). The viability of cells is measured after 24 hours (ADM) and 48 hours (ADM) by a MTT test (Alley M. C., Scudero D. A. et al. - Cancer REsearch -48, 589-1988. The results are expressed in percentage of control cells viability, that is to say cells incubated without drugs. This study has been carried out at least in triplicate.

C. C-20'-DEOXY C-20'-DEETHYL VINCOVALINE (n° 352) AND $P_{388}R$

Modulator cytotoxicity

The incubation during 24 hours and 48 hours of $P_{388}S$ and $P_{388}R$ cells with increasing concentrations of modulators does not involve any cytotoxicity with concentrations up to 25 $\mu M$ for sensitive cells and 100 $\mu M$ for resistant cells (FIG. 15).

Sensitization of $P_{388}R$ cells to antitumorous agents with D-DEV modulator

The $P_{388}R$ cells are incubated at 37° C. during 24 hours with constant subtoxic concentrations of antitumoral drugs and increasing concentrations of modulators from 1 to 100 $\mu M$.

The sensitization of $P_{388}R$ cells to a cytotoxic activity of antitumorous drugs (ADM VBL and VCR) with D-DEV modulator (n° 352) is shown in FIG. 16 to 18.

The modulator effect is dependent on D-DEV concentrations (n° 352) and cytotoxic agent concentrations. For instance, FIG. 16 shows that the modulator at a 100 $\mu M$ concentration has no effect when ADM is used at 0.17 $\mu M$. By contrast, when the concentration of antitumoral compound is 10-fold above (1.72 $\mu M$) the percentage of cellular survival is only 50% with a concentration of D-DEV (n° 352) at 30 $\mu M$.

SUMMARY OF FIGURES

FIG. 1 represents binary vinca alkaloid-type compounds examined in this study.

BIBLIOGRAPHY

Figure 2C:
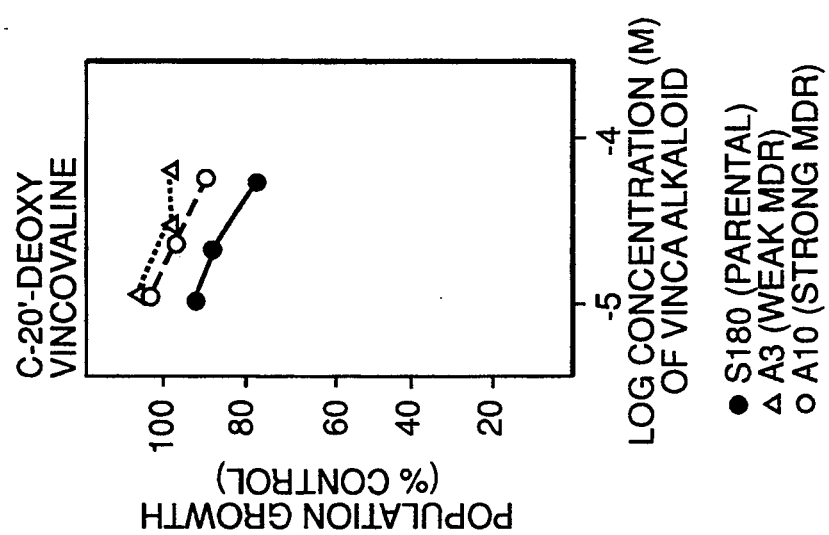
FIG. 2 represents the toxicity of the vinca alkaloid compounds to population growth. Vindoline, vincovaline or the analog, C-20'-deoxy vincovaline was added, at various concentrations, to S180 (●), A3 (o), or A10 (Δ) cell cultures. The population cell number was determined 72 hours later.
Figure 2B:
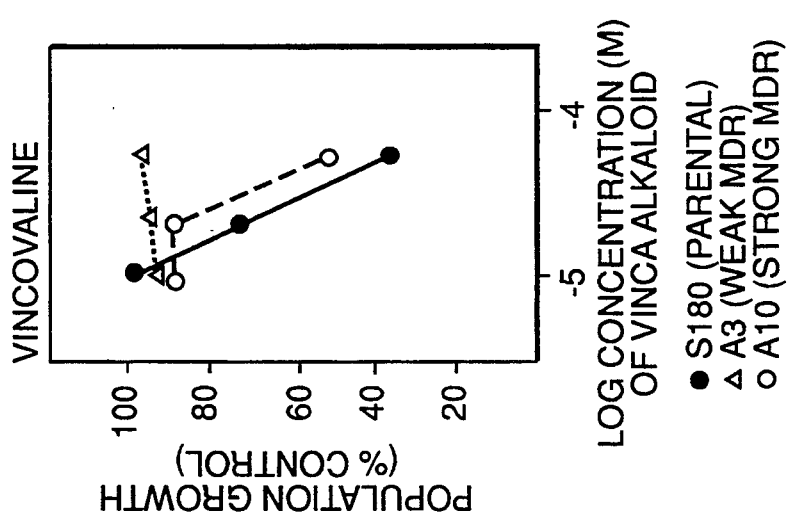
Figure 2A:
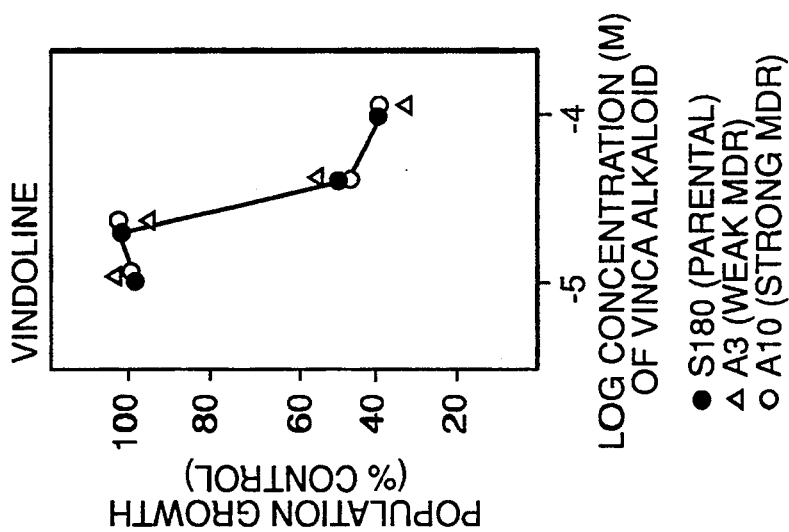
Figure 3:
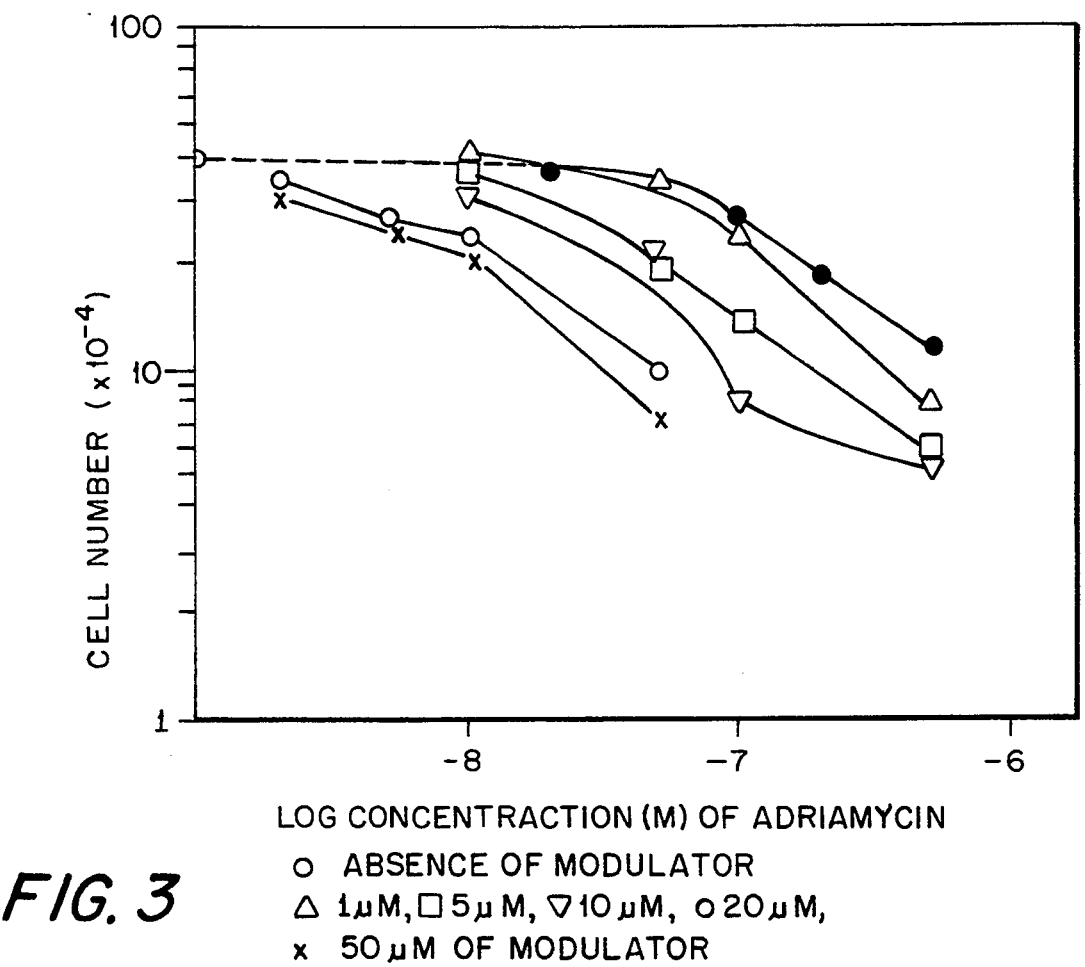
FIG. 3 represents the modulation of the sensitivity of S180 cells to ADM by the congener, C-20'-deoxy vincovaline. The effect of ADM on population growth was determined in the absence (●), or the presence of 1 $\mu M$ (Δ), 5 $\mu M$ (□), 10 (∇), 20 $\mu M$ (o), or 50 $\mu M$ (X) of the congener.
Figure 8:
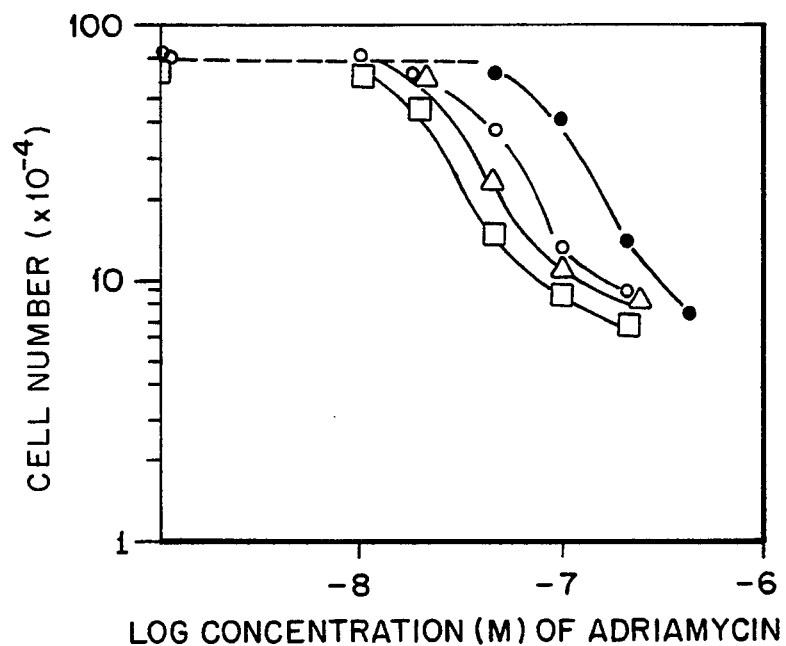
FIG. 8 represents the modulation of ADR sensitivity in the parental S180 cell line by the analog C-20'-deoxy deethyl vincovaline. Population growth after 72 hours of incubation was determined in the absence (•), or the presence of 8 μM (o) 10 μM (Δ) or 40 μM (□) of the anlog. Data presented are the averages of duplicate samples from two separate experiments. S.D. $\leq 10\%$.
Figure 4A:
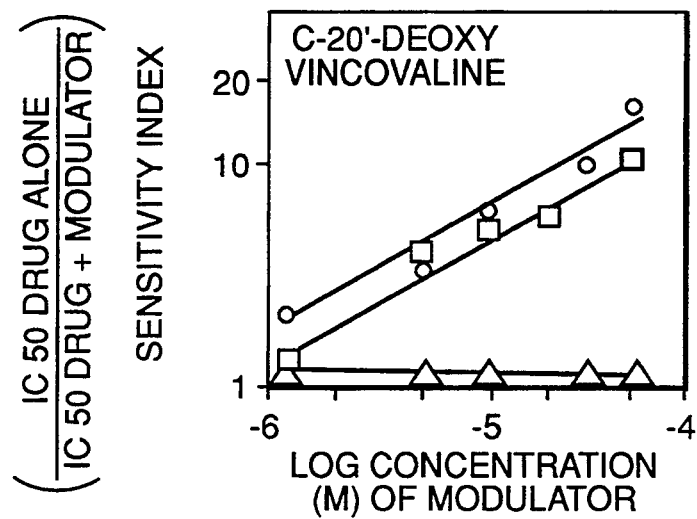
FIG. 4 represents the potency of the vinca alkaloid compounds as modulators of drug sensitivity in S180 cells. The enhancement of sensitivity was calculated as the sensitivity index=IC50 of the drug alone divided by the IC50 of the drug+modulator. The IC50s for ADM (o) VBL (Δ), or VCR (□) were determined over a concentration range of each modulator from data such as those depicted in FIG. 3. The values presented were averaged from duplicate samples of two separate experiments, S.D. <15% of the mean.
Figure 4B:
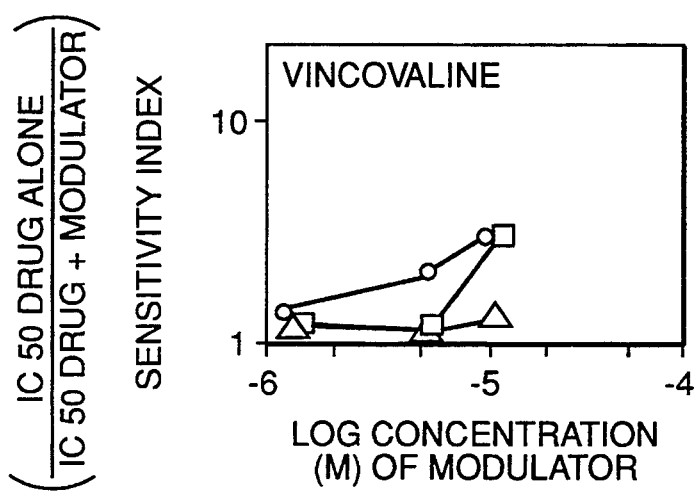
Figure 4C:
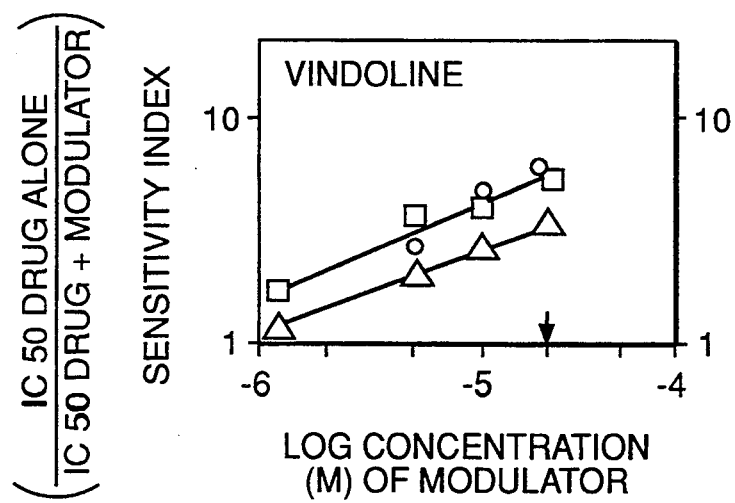
Figure 5A:
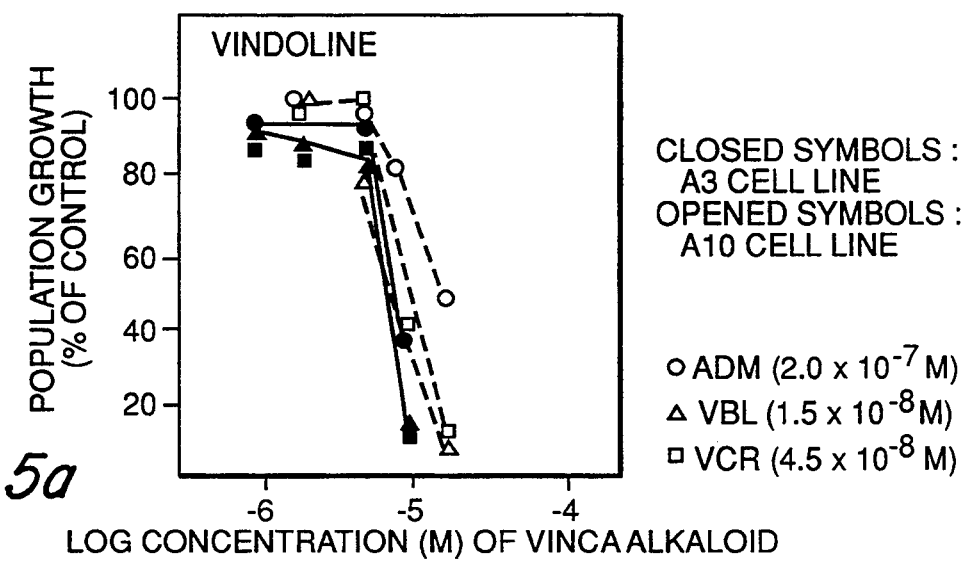
FIG. 5 represents the modulation of multidrug resistance in the MDR cell strains by the vinca alkaloids. Vindoline (A), vincovaline (B), or the analog C-20'-deoxy vincovaline (C) was added, at various concentrations, to A3 (closed symbols) or A10 (opened symbols) cell cultures containing the parental IC70 of each drug: $2.0 \times 10^{-7}M$. ADM (circles: $1.5 \times 10^{-8}M$ VBL (triangles); and $4.5 \times 10^{-8}M$; VCR (squares). Population growth was determined 72 hours later.
Figure 5B:
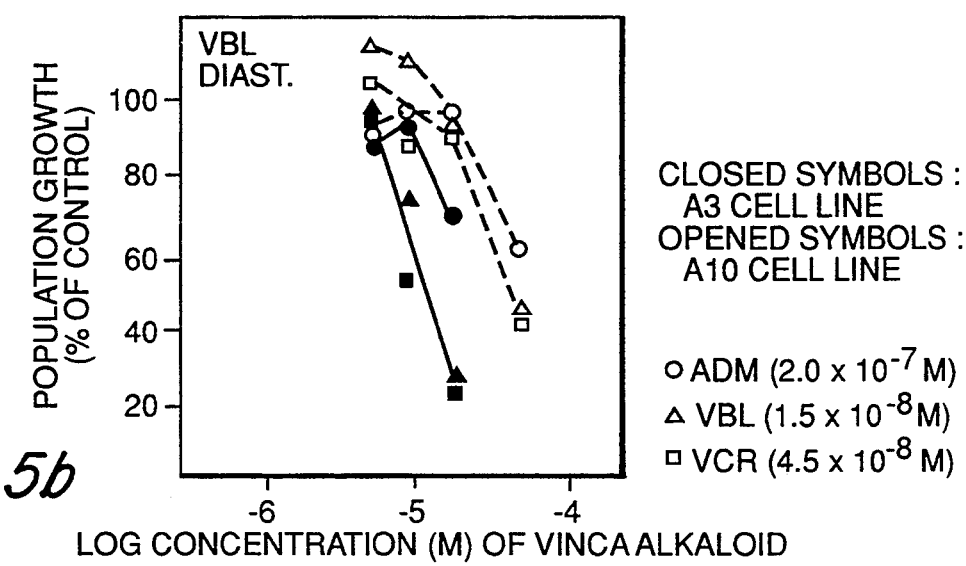
Figure 5C:
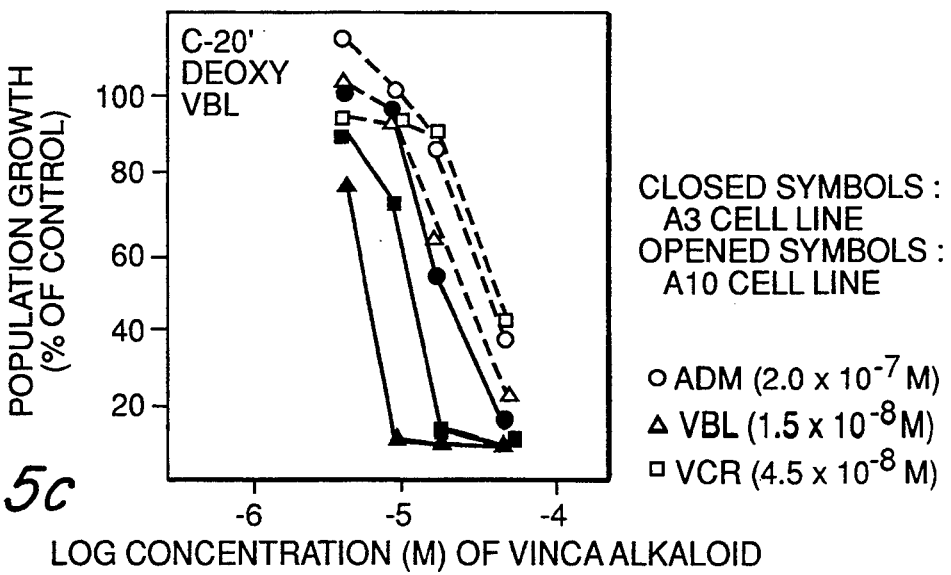
Figure 6A:
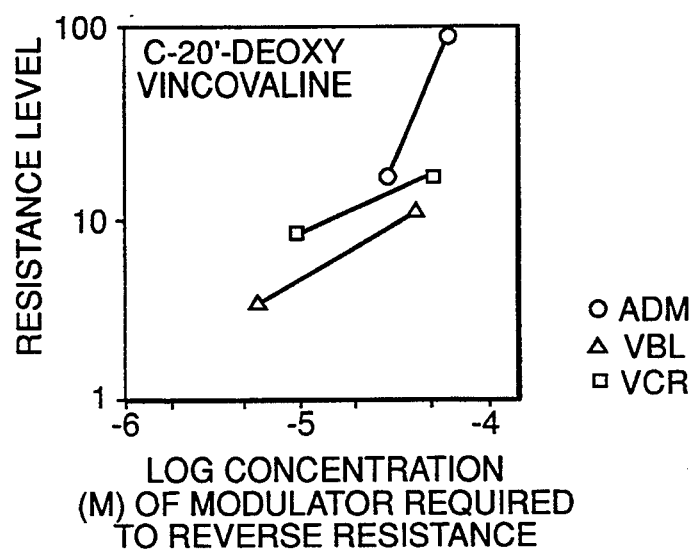
FIG. 6 represents the relationship between cellular drug resistance level and the minimal modulator concentration required for complete reversal of drug resistance. The drugs examined were ADM (o), VBL (Δ), and VCR (□). The amount (concentration) of modulator, necessary to reverse each level of drug resistance contained in the A3 and A10 cell lines, was determined from data such as those of FIG. 5. The values presented were averaged from duplicate samples of two separate experiments, S.D.<15% of the mean. The arrows denote the non-toxic concentration limit for the modulator; in the case of Vincovaline this value is dependent on the MDR cell strain, $2\times10^{-5}$M, A3; $5\times10^{-5}$M. A10.
Figure 6B:
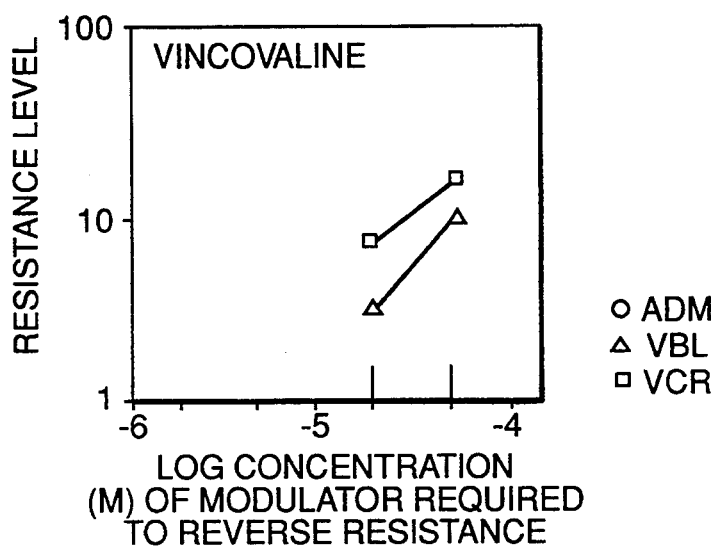
Figure 6C:
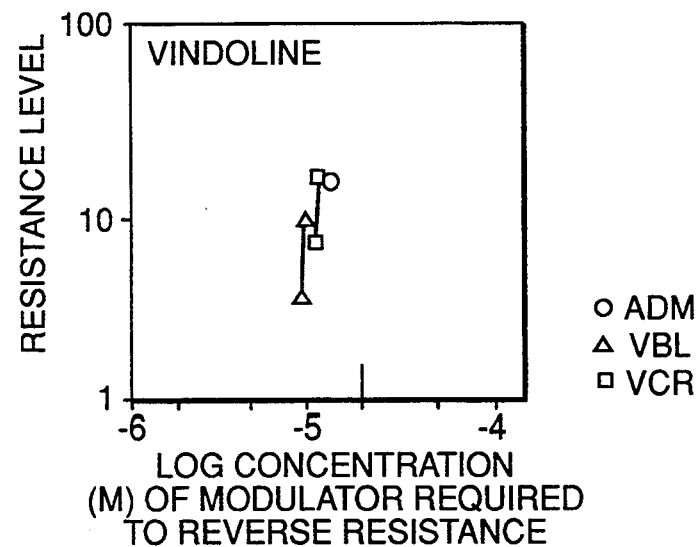
Figure 7A:
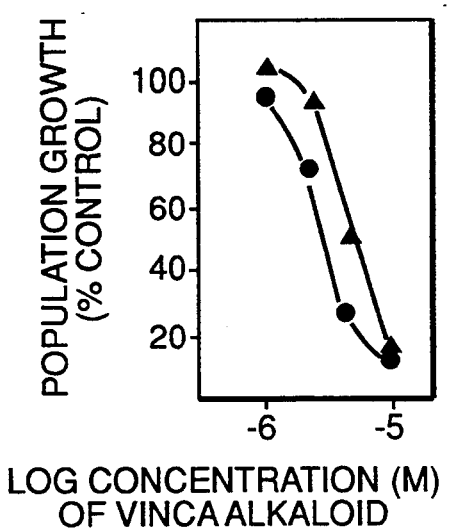
FIG. 7 represents the toxicity of analog C-20'-deoxy vincovaline (A) and C-20'-deoxy deethyl vincovaline (B) to population growth of the rat colon adenocarcinoma cell lines. The congener was added at various concentrations to RCC-2 (•) and RCC-5 (▲) cell cultures and the population cell number was determined 72 hours later. Data is presented from a typical experiment. Please note the values for analog concentration on the abscissa.
Figure 7B:
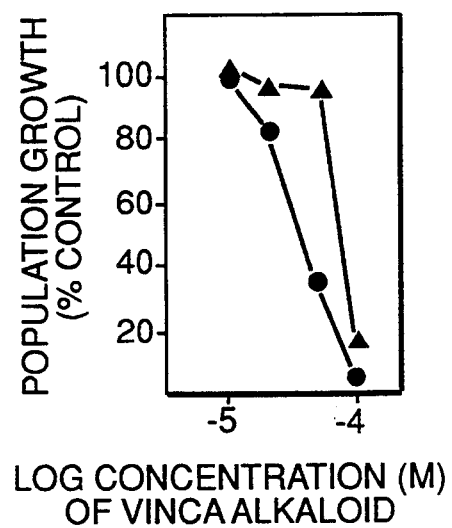
Figure 9A:
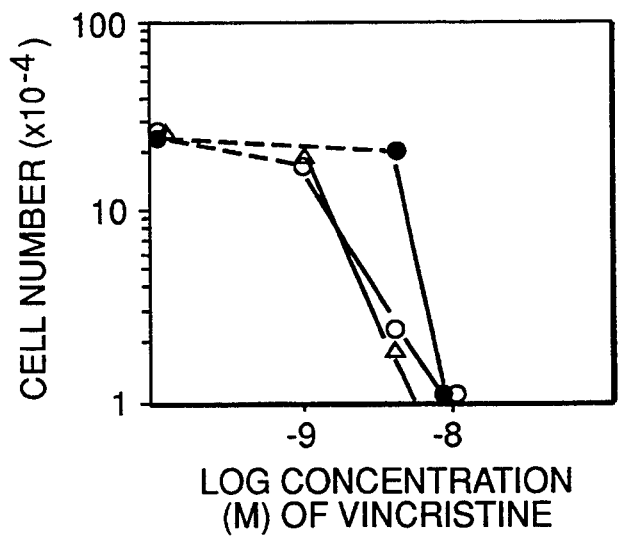
FIG. 9 represents the modulation of VCR sensitivity in the RCC-12 (A) and RCC-5 (B) cell lines by the analog C-20'-deoxy deethyl vincovaline. Population growth was determined after 72 hours incubation in the absence (o), or presence of 10 μM (o), 20 μM (Δ), or 50 μM of analog. Data presented are from a typical experiment.
Figure 9B:
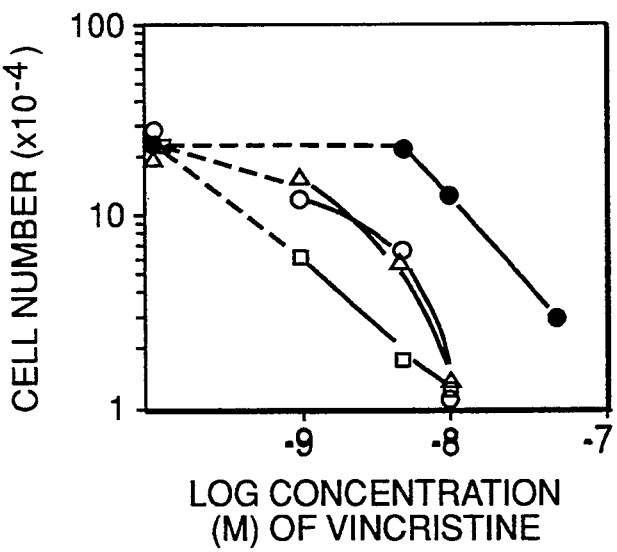
Figure 10A:
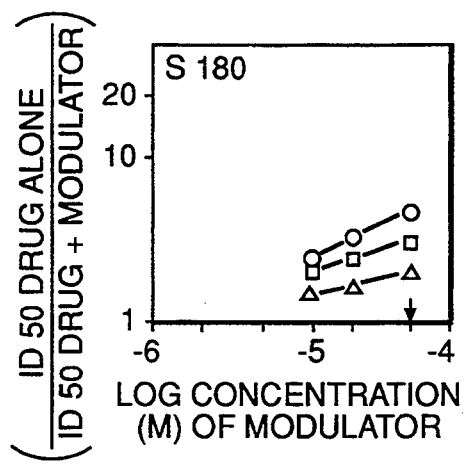
FIG. 10 represents the potency of the analog C-20'-deoxy deethyl vincovaline as a modulator of the drug sensitivity of various cell lines: the parental S180 cell line: the two rat colon cancer cell lines, RCC-2 and RCC-5; and the human epidermoid carcinoma cell line KB-3-1 and its MDR cell strain KB-V1, which expresses very high levels of drug resistance (200-500 fold). The enhancement of sensitivity was calculated as the sensitivity index $=IC_{50}$ of the drug alone divided by the $IC_{50}$ of the drug+analog. The drugs examined were ADM (o), VBL (Δ), and VCR (□). The $IC_{50}$ values for the S180 and RCC cell lines were determined from population experiments such as those shown in FIGS. 8 and 9. The cytotoxicity of drug and analog treatments in the KB cell lines were measured by cloning efficiencies. The arrows denote the non-toxic concentration limit of the analog in each cell line.
Figure 10B:
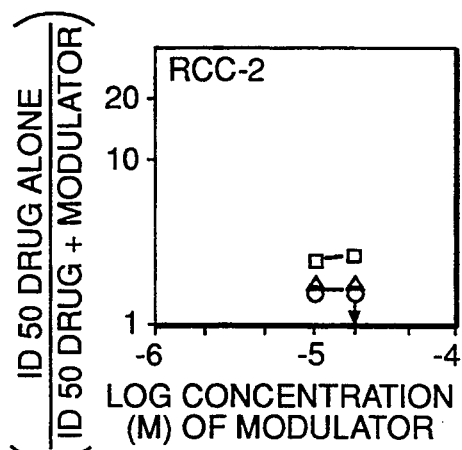
Figure 10C:
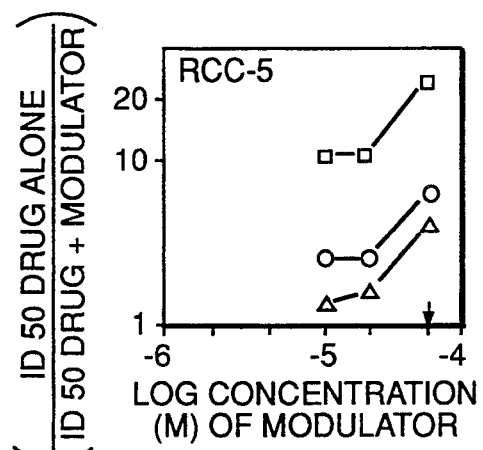
Figure 10D:
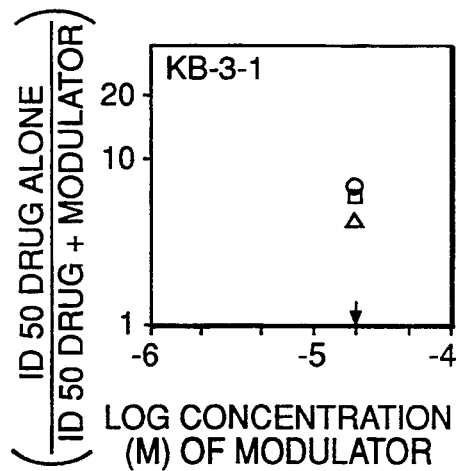
Figure 10E:
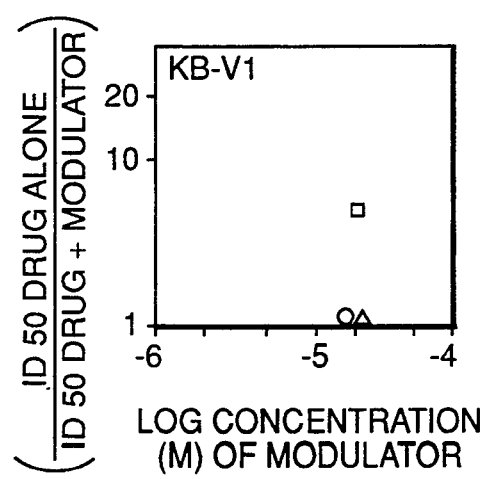
Figure 11:
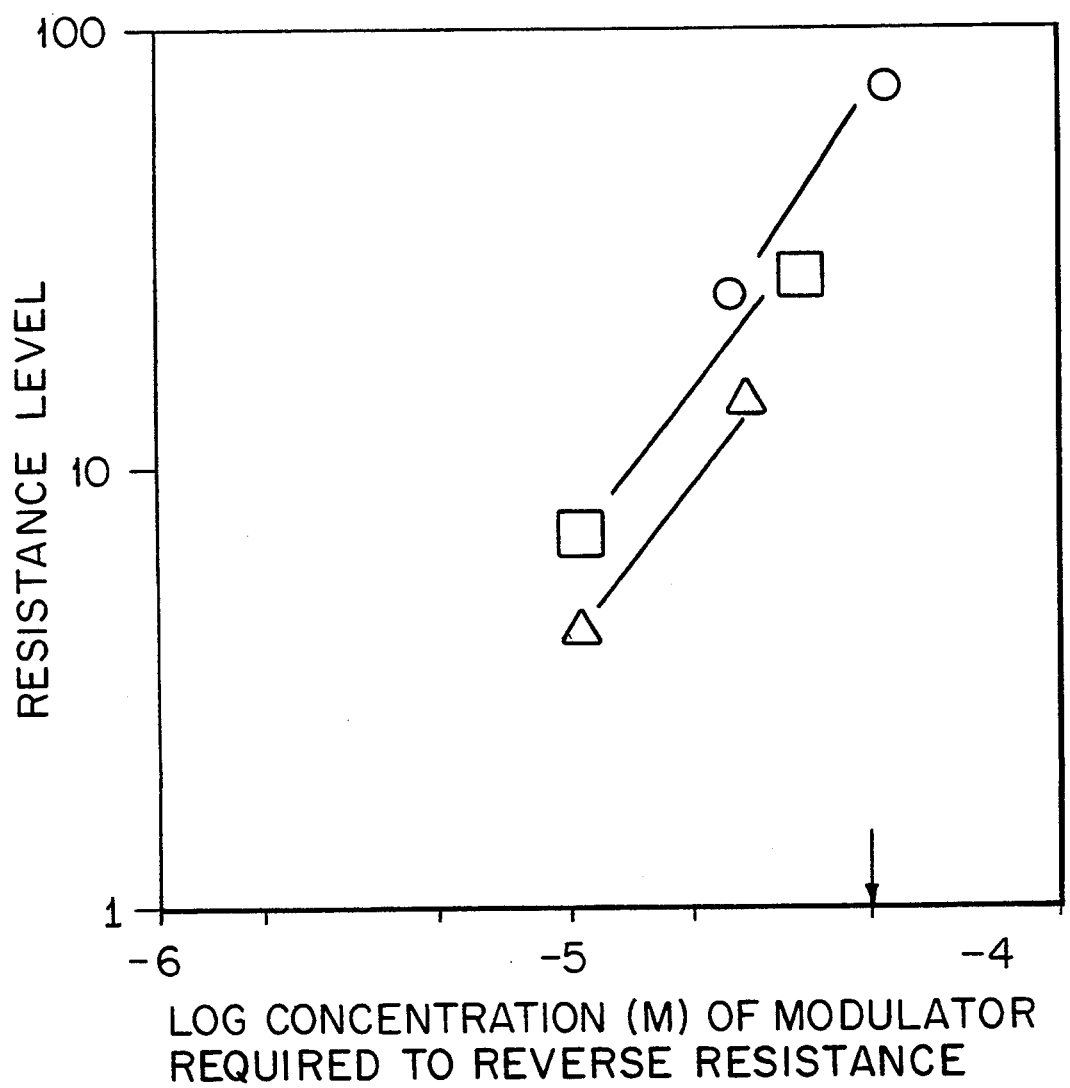
FIG. 11 represents the modulation of multidrug resistance in the S180 MDR cell strains A3 and A10. The cellular drug resistance level is plotted against the minimal concentration of C-20'-deoxy deethyl vincovaline required for the complete reversal of drug resistance to ADM (o), VBL (Δ), and VCR (□). In the case of high level ADM resistance (Δ), the sensitivity of the cells was restored to 80% of the parental value. The arrow denotes the non-toxic concentration limit of the analog.
Figure 12:
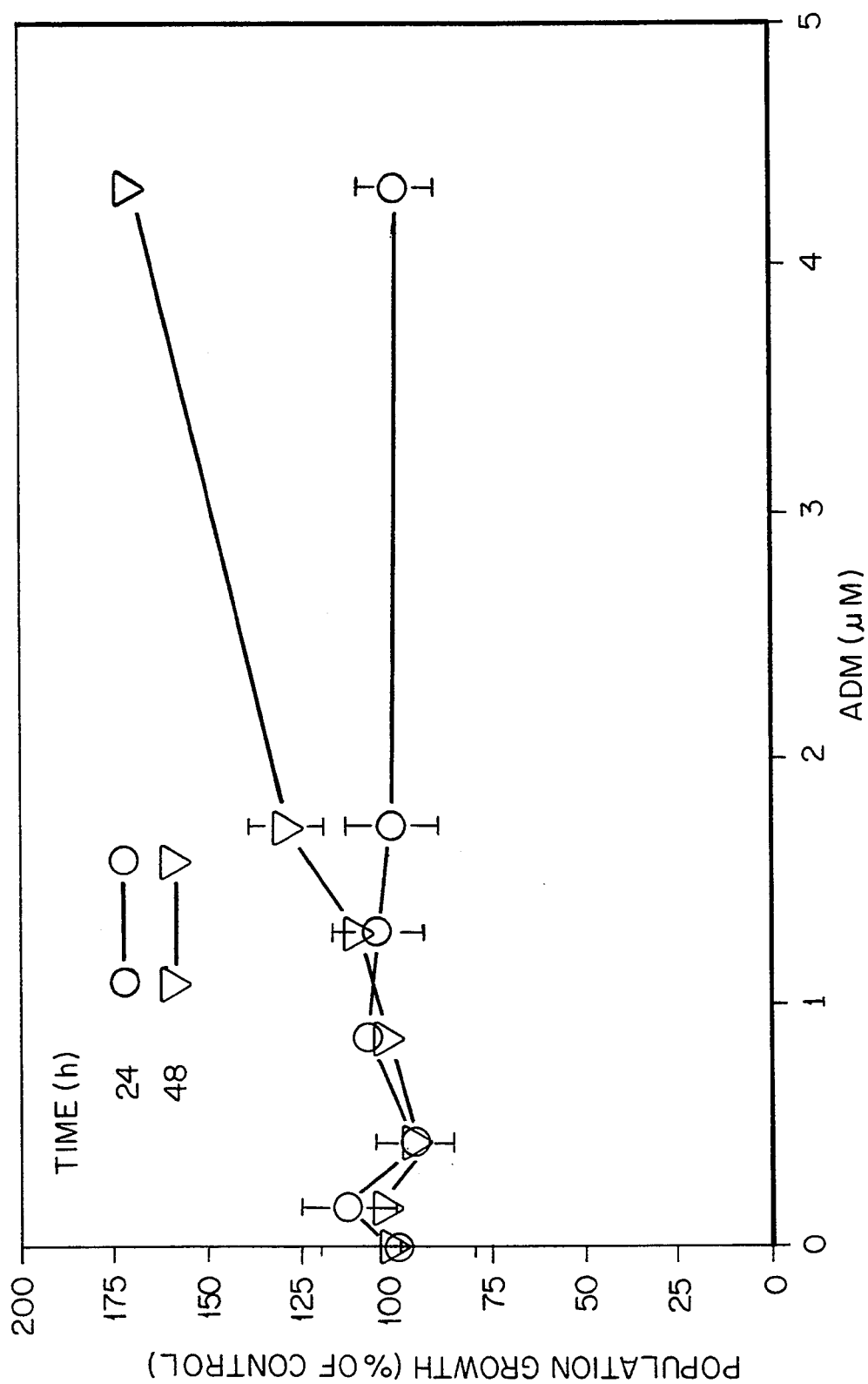
FIG. 12 represents the lack of adriamycin cytotoxicity in $P_{388}R$ cells after an incubation at 37° C. during 24 and 48 hours between ADM concentrations from 0.17 to 4.31 μM.
Figure 13:
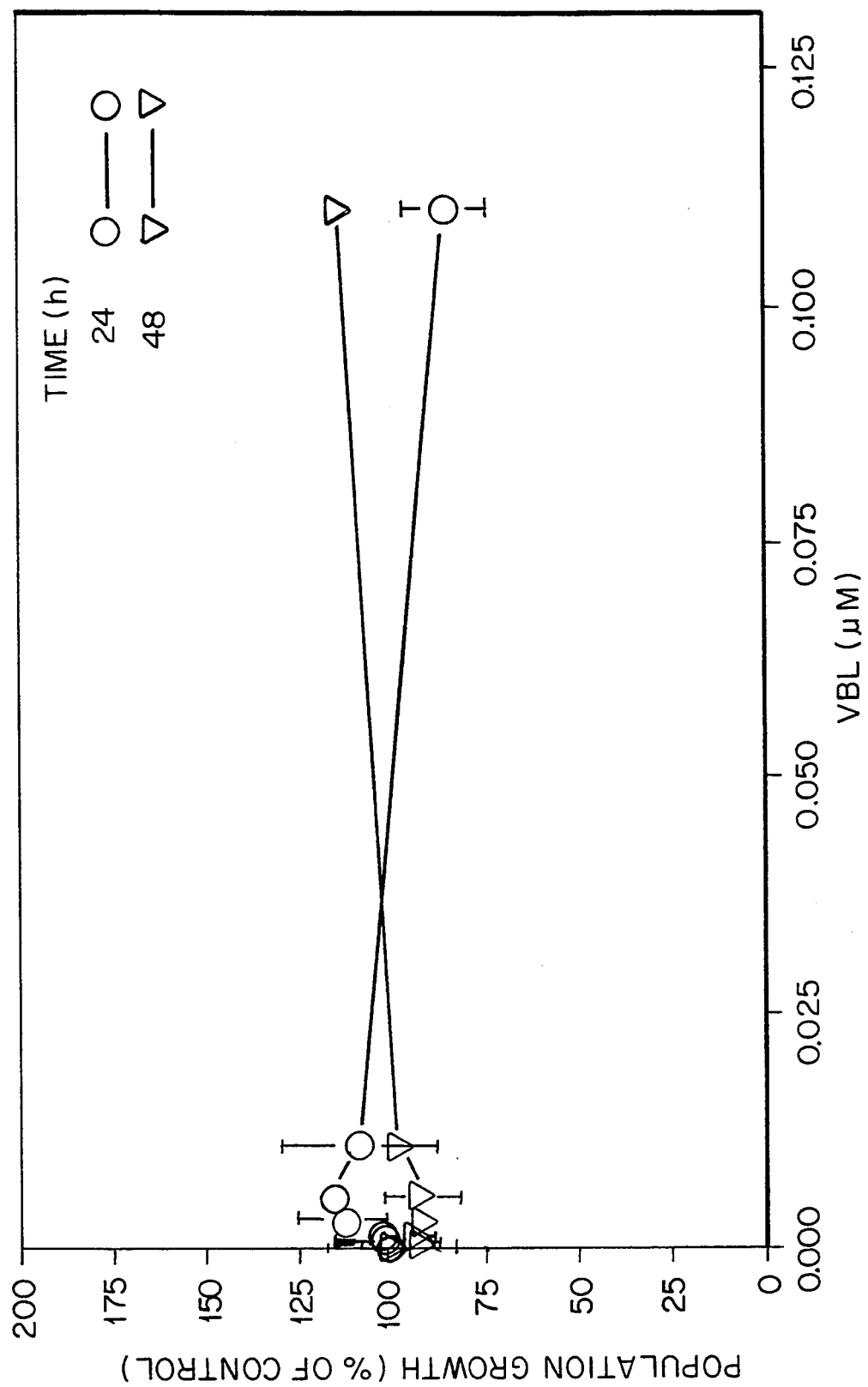
FIG. 13 represents the lack of vinblastine cytotoxicity at concentrations from 0.00055 to 0.11 μM towards $P_{388}R$ cells after incubation during 24 hours.
Figure 14:
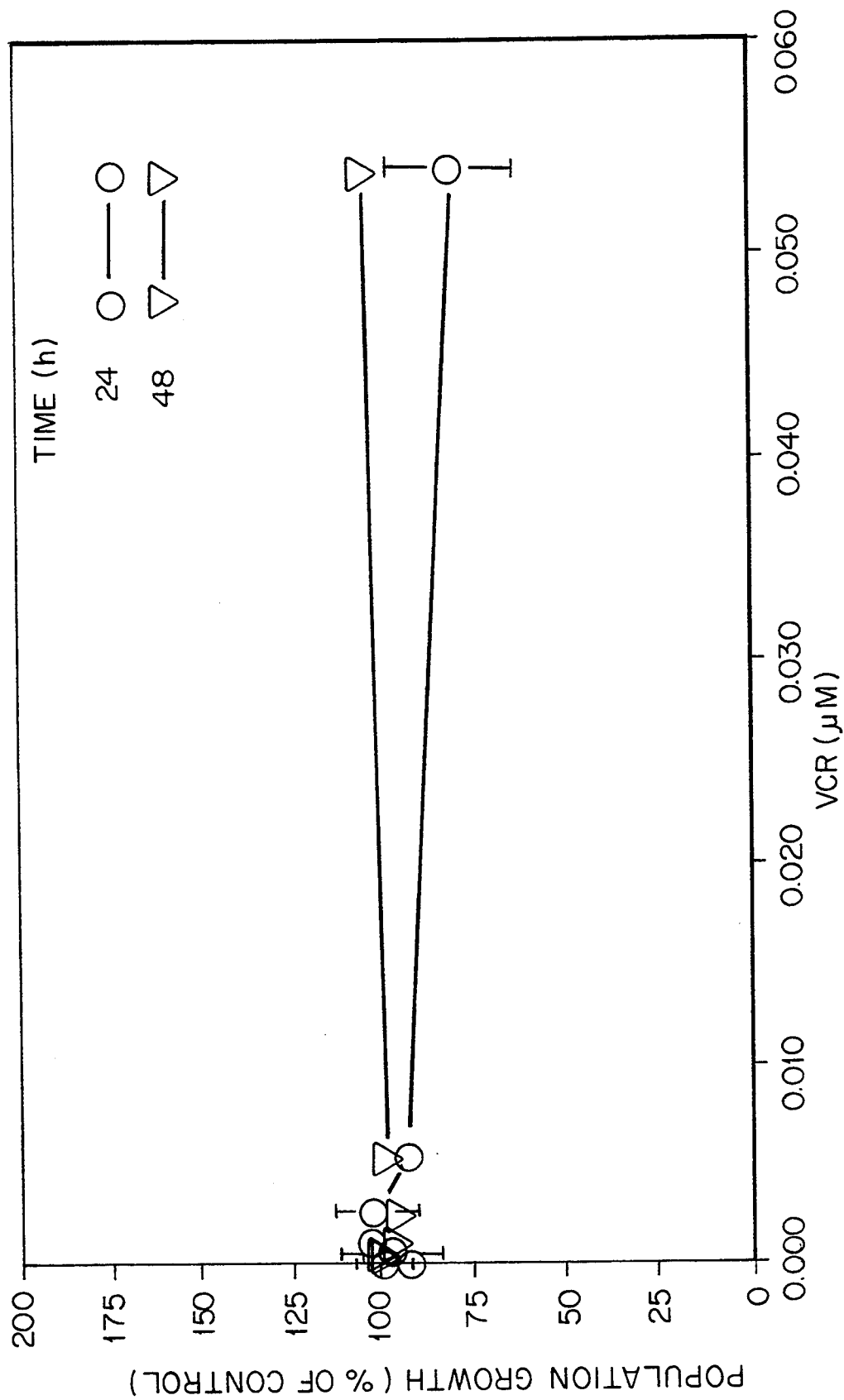
FIG. 14 shows the lack of vincristine cytotoxicity at concentrations comprised between 0.1 nM and 0.054 μM towards $P_{388}R$ cells after incubation during 24 hours.
Figure 15:
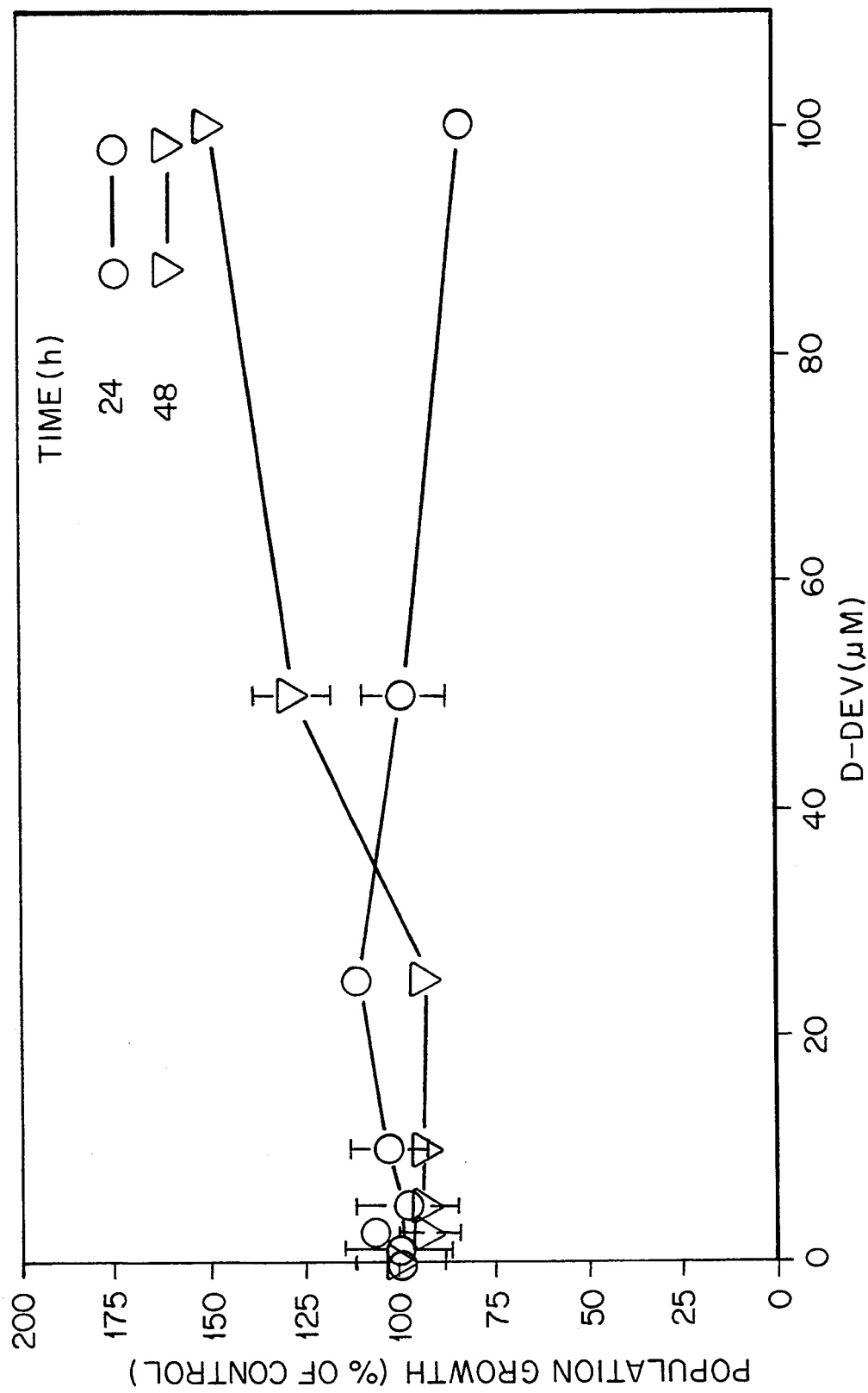
FIG. 15 represents the lack of C-20'-deoxy C-20'-deethyl vincovaline (compounds n° 352 D-DEV) cytotoxicity on $P_{388}R$ cells up to 100 μM concentrations after incubation during 24 and 48 hours.
Figure 16A:
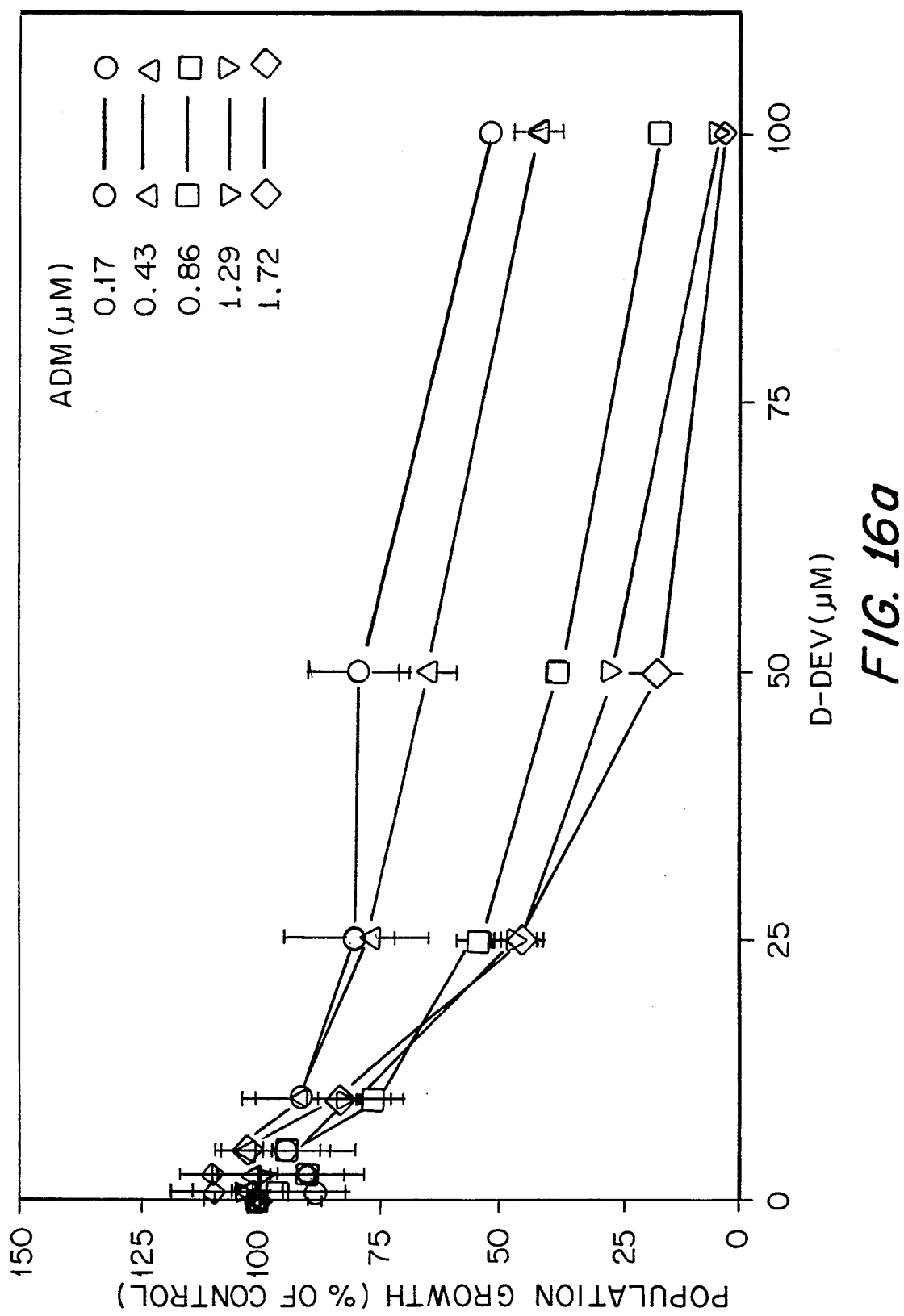
FIG. 16 represents the sensitization of $P_{388}R$ cells by compound n° 352, used at increasing concentrations, to the drug ADM used at concentrations of (o) 0.17 μM
(Δ) 0.43 μM
(□) 0.86 μM
(∇) 1.29 μM
( ) 1.72 μM after $\geq$ hours (FIG. 16a)
after 48 hours (FIG. 16b)
Figure 16B:
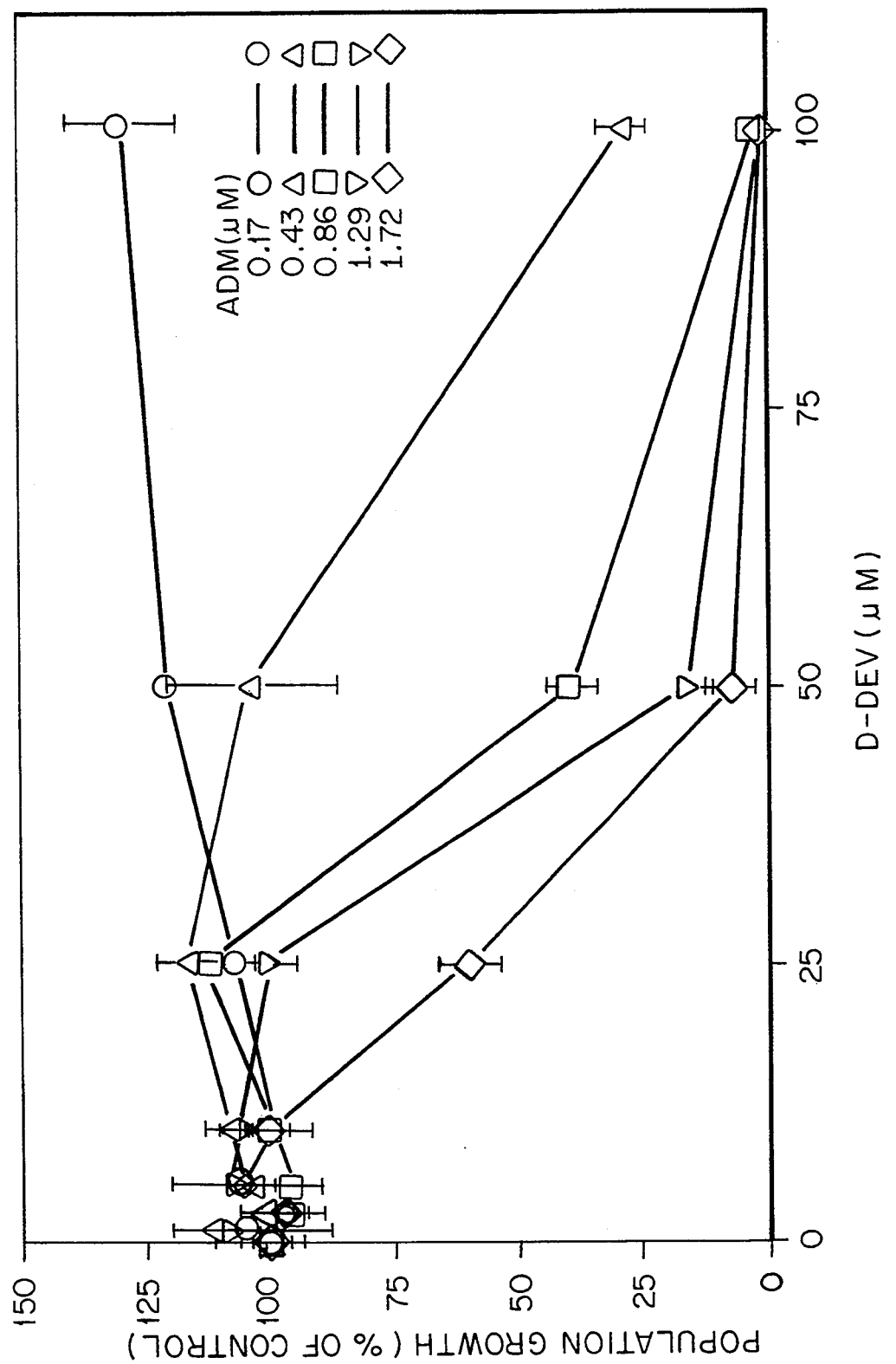
Figure 17:
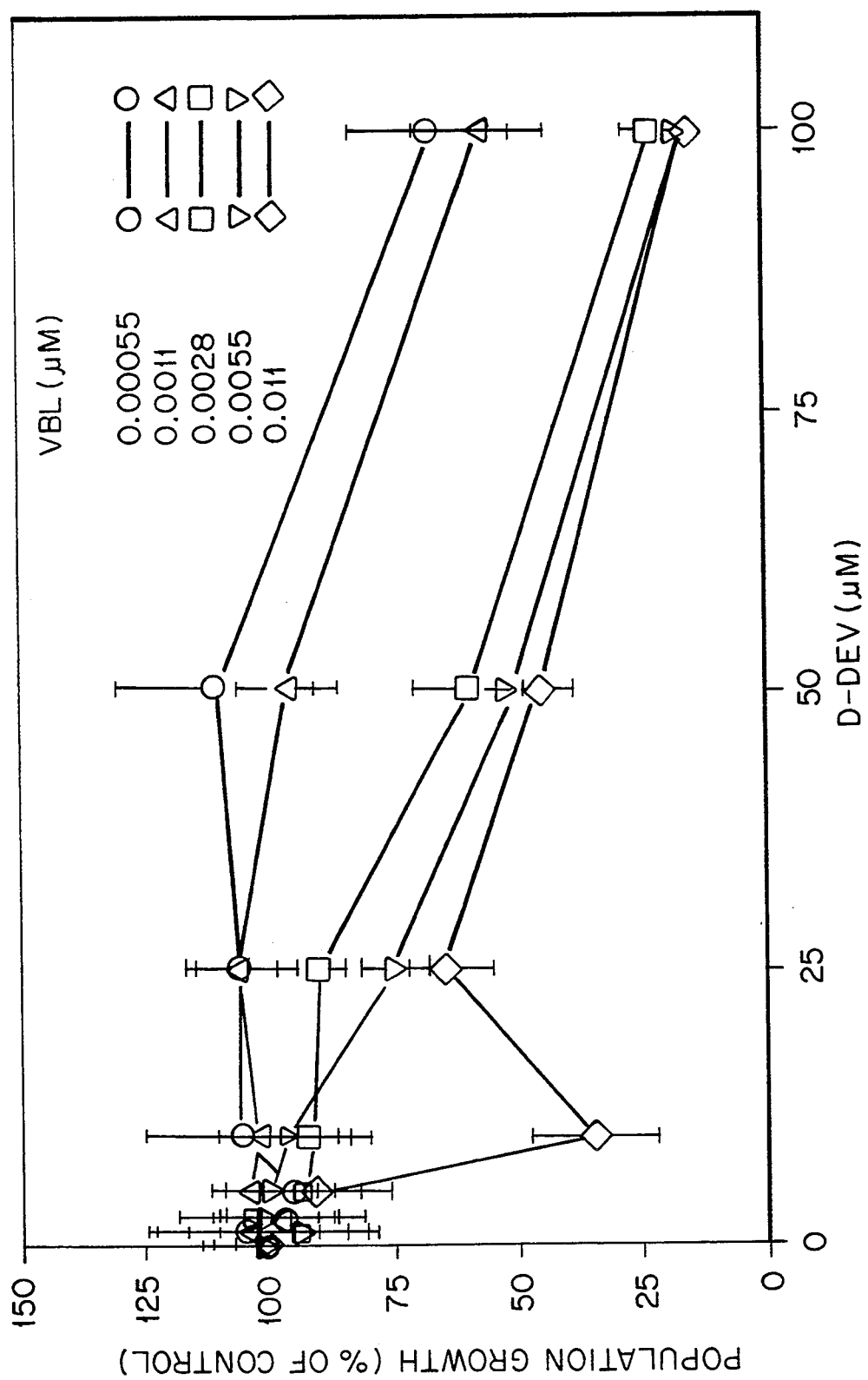
FIG. 17 shows the sensitization of $P_{388}R$ cells to vinblastine (24 hours) by compound n° 352. The VBL concentrations are (o) 0.55 nM
(Δ) 1.1 nM
(□) 2.8 nM
(∇) 5.5 nM
( ) 0.011 μM
Figure 18:
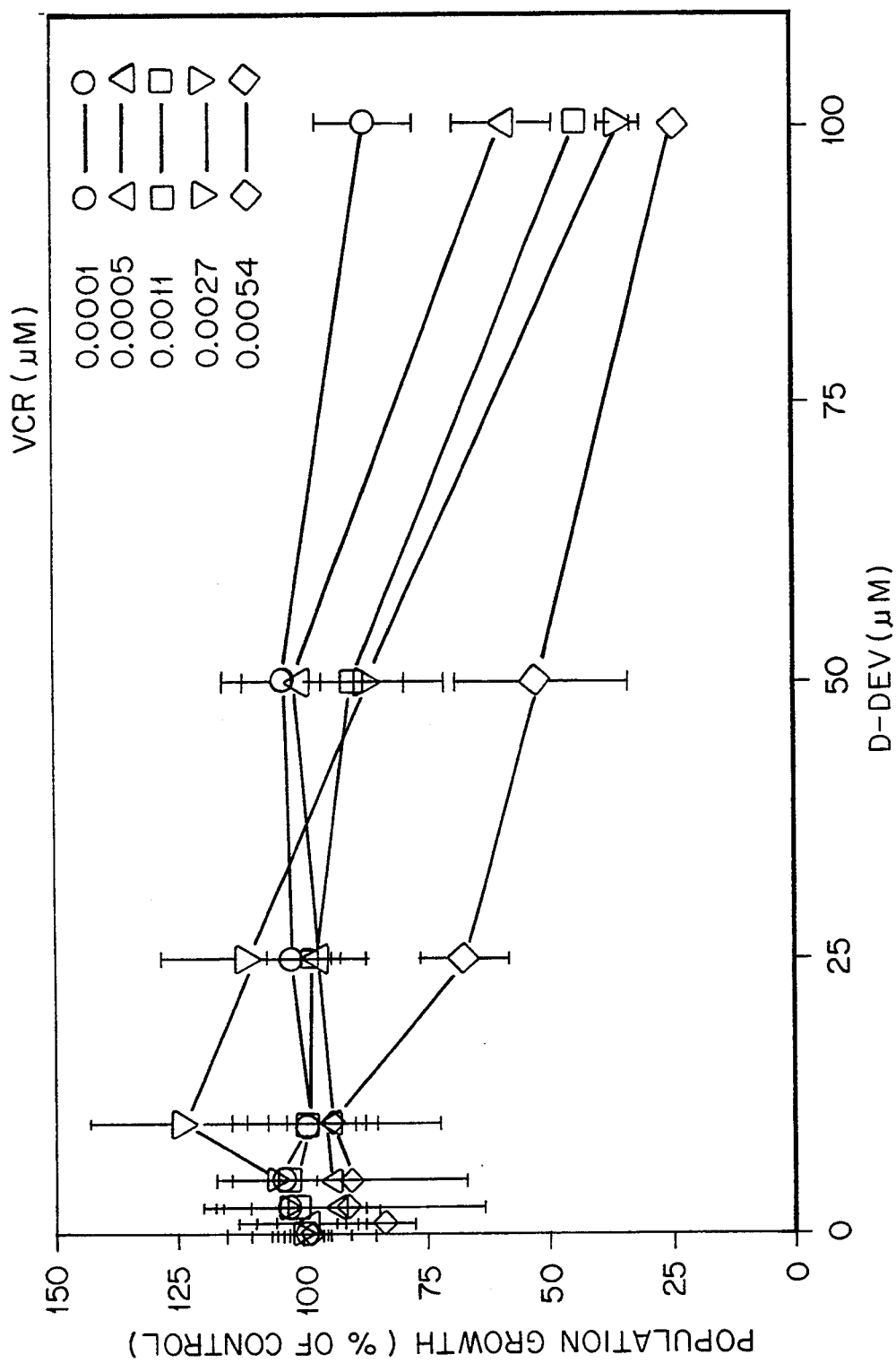
FIG. 18 shows the sensitization of $P_{388}R$ cells to vincristine (24 hours) by the compound n° 352. The VCR concentrations are (o) 0.1 nM
(Δ) 0.5 nM
(□) 1.1 nM
(∇) 2.7 nM
( ) 5.4 nM

1. Ozols. R. F. and Cowan K. New aspects of clinical drug resistance. The role of gene amplification and the reversal of resistance in refractory cancer. In: DeVita. V. T., Hellmann. S., Rosenberg. S (eds). Important Advances in Oncology pp 129–158. Philadelphia, Lippincott 1986.

2. Bradley, G., Juranka. P. F., and Ling, V. Mechanism of drug resistance. Biochim. Biophys. Acta. 948. 81–128. 1988.

3. Pastan. I. H., and Gottesman, M. M. Molecular biology of multidrug resistance in human cells. In: DeVita, V. T., Hellmann. S., Rosenberg, S., (eds) Important Advances in Oncology, pp3–16. Philadelphia. Lippincott. 1988.

4. Tsuruo. T., Iida. H., Tsukagoshi. S., and Sakurai. Y. Increased accumulation of vincristine and adriamycin in drug resistant P388 tumor cells following incubation with calcium antagonists and calmodulin inhibitors. Cancer Res. 42:4730–4733. 1982.

5. Inaba. M., Fujikura. R., Tsukagoshi, S., and Sakurai, Y. Restored in vitro sensitivity of adriamycin and vicristine resistant P388 leukemia with reserpine. Biochem. Pharmacol. 30: 2191–2194, 1981.

6. Aklyama, S-i., Shiraishi, N., Kuratomi, Y., Nakagawa, N. M., and Kuwano, M. Circumvention of multiple-drug resistance in human cancer cells by thioridazine, trifluoperazine and chlorpromazine, J. Natl. Cancer Inst. 76:839–844, 1986.

7. Nakagawa, M., Akiyama, S-i, Yamaguchi, T., Shiraishi, N., Ogata, J., and Kuwano, M. Reversal of multidrug resistance by synthetic isoperenoids in the KB human cell line. Cancer Res. 46:4453–4457, 1986.

8. Willingnam, M. C., Cornwell, M. M., Cardarelli. C. O., Gottesman, M. M., and Pastan, I. Single cell analysis of daunomycin uptake and efflux in multidrug-resistant and sensitive KB cells: Effects of verabamil and other drugs. Cancer Res. 46:5941–5946, 1986.

9. Inaba, M., Nagasnima, K., Sakurai, Y., Fukui, M., and Yanagi, Y. Reversal of multidrug resistance by non-antitumor anthracycline analogs, Gann 75:1049-1052. 1984.

10. Inaba. M., and Nagashima, K. Non-antitumor vinca alkaloids reverse multidrug resistance in P388 leukemia cells in vitro, Gann. 77: 197-204, 1986.

11. Kuehne, M. E., Zebovitz, T. C., Bornmann, W. C., and Marko, I. Three routes to the critical C16'-C/4' part relative stereochemistry of vinblastine. Syntheses of 20'-deethyl-20'-deoxyvinblastine and 20'-deethyl-20'-deoxyvincovaline, J. Org. Chem. 52:4340-4349, 1987.

12. Kuenne, M. E. and Bornmann, William G. Syntheses of 20'-Deoxyvinblastine. 20'-Deoxyleurosidine, 20'-Deoxyvincovaline, 20'-epi-20'-Deoxyvincovaline and 20'-Deoxyvincristine and its 20'-Epimer through Racemic and Enantioselectively Generated Intermedites. J. Org.Chem. 54:3407-3420, 1989.

13. Tsuruo, T., Iida, H., Tsukagoshi., S., and Sakurai, Y. Overcoming of vincristine resistance in P388 leukemia in vivo and in vitro through enhanced cytotoxicity of vincristine and vinblastine by verapamil. Cancer Res. 41:1967-1972, 1981.

14. Tsuruo, T., Tsukagoshi. S., and Sakurai. Y. Increased accumulation of vincristine and adrramycin in drug-resistant P388 tumor cells following incubation with calcium antagonists and calmodulin inhibitors. Cancer Res. 42:4730-4733, 1982.

15. Borman, L. S., Littlefield, L. G. and Swartzendruber, D. C. Establishment of two parental cell lines and three clonal cell strains from rat colonic carcinoma. Cancer Res. 42:5074-5083, 1982.

16. Shen. D-W., Cardarelli, C., hwang, J., Cornwell, M., Richert, N., Ishii, S., Pastan, I., and Gottesman, M. M. Multiple drug-resistant human KB carcinoma cells independently selected for high-level resistance to rolchicine adriamvcin or vinblastine, J. Biol. Chem. 261:7762-7770, 1986.

17. Siegiriea. J. M., Tritron. T. R. and Sartoreli. A. C. Comparison of anthracycline concentrations S180 cell lives of varving sensitivity. Eur, J. cancer Clin. Oncol. 19:1133-1141. 1983.

18. Zamora. J. M. Pearce, H. L. and Beck. W. T. Physical-chemical properties shared by compounds that modulate multidrug resistance in human leukemia cells. Molec. Pharmacol. 33:454-462. 1988.

19. Yamashita, N., Hamada, H., Tsuruo. T. and Ogate. E. Enhancement of voltage gated Na channel current associated with multidrug resistance in human leukemia cells. Cancer Res. 47:3736-3741, 1987.

20. Lee, S. C., Deutsch, C., and Beck, W. T. Comparison of ion channels in multidrug-resistant and -sensitive human leukemia cells. Proc. Natl. Acad. Sci., USA 85:2019-2023. 1988.

21. Beck, W. T., Cirtain, M. C., Look, A. T., and Ashmun. R. A. Reversal of vinca alkaloid resistance but not multiple drug resistance in human leukemia cells by verapamil. Cancer Res. 46:778-784, 1986.

22. Fojo, A. T., Ueda, K., Slamon, D. J., Poplack, D. G., Gottesman, M. M., and Pastan, I. Expression of a multidrug-resistance gene in human tumors and tissues Proc. Natl. Acad. Sci., USA 84:265-269. 1987.

23. Thiebaut, F., Tsuruo. T., Hamada, H., Gottesman, M. M., Pastan, I., and Willingham, M. C. Cellular Localization of the multidrug-resistance gene product P-glycoprotein in normal human tissues. Proc. Natl. Acad. Sci., USA 84:7735-7738, 1987.

24. P. Potier, N. Langlois. Y. Langlois and F. Gueritte, J. Chem. Soc., Chem. Commun., 670 (1975).

25. N. Langlois, F. Gueritte, Y. Langlois and P. Potier, J. Am. Chem. Soc., 98.7017 (1976).

26. P. Potier, Ann. Pharm. Fr., 38. 407 (1980).

27. P. Potier. J. Nat. Prod., 43. 72 (1980).

28. J. P. Kutney, Lloydia, 1977, 40, 107.

29. J. P. Kutney, A. H. Ratenffe, A. M. Treasurywala and S. Wunderly Heterocycles. 3, 639 (1975).

30. J. P. Kutney. P. Hibino, E. Jahngen, T. Okutani, A. H. Ratchiffe, A. M. Treasurywala and S. Wunderly, Helv. Chim. Acta. 59. 2858 (1976).

31. J. P., Kutney, J. Beck, F. Bvlsma and W. J. Cretwey, J. Am. Chem. Soc., 90. 4504 (1968). 32.J. P. Kutney, J. Beck, F. Bylsma, J. Cook, W. J. Cretney, K. Fuji, R. Imnof. A. M. Treasurywala. Helf. Chim. Acta. 58. 1690 (1975).

33G. Schill, C. V. Priester, U. F. Windhovel and H. Fritz, Helv. Chim. Acta. 69.438 (1986).

34. g. Schill, U. P. Ulrich, F. Udo, H. F. Windhovel, L. Hartmut, Tetranedron, 43. 3729 (1987). 35. G. Schill, U. P. Claus, F. Udo. H. F. Windhovel, ibid. 43. 3741. 3765(1987).

36. Carey and Kuehne, Journ, of Org. Chem. Vol. 47, n° 10. 3811 1982. A proposal for specifying relative configuration.

What we claim is:

1. A method for sensitizing, in a patient in need thereof, tumoral cells to vinca alkaloid or antibiotic chemotherapy anticancerous drugs or reversing the tumoral cells resistance to vinca alkaloid or antibiotic chemotherapeutic antitumoral drugs or both, which comprises administering to said patient an enhancer agent in an amount effective to sensitive said tumoral cells to vinca alkaloid or antibiotic chemotherapeutic anticancerous drugs or to reversing the tumoral cells resistance to vinca alkaloid or antibiotic chemotherapeutic antitumoral drugs or both; wherein said enhancer agent is a binary vinca alkaloid, analog to vinblastine or vincristine, with a low cytotoxicity or devoid of cytotoxicity, wherein said enhancer agent has the following Formula I:

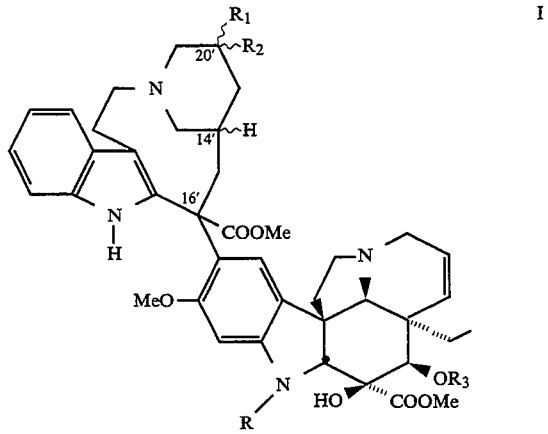

wherein
R=formyl or methyl ($R_1$, $R_2$)=(H, ethyl), (H,H), (Methyl, H) or (Methyl, Methyl).
$R_3$=H or acetyl.

2. A method for sensitizing, in a patient in need thereof, tumoral cells to vinca alkaloid or antibiotic chemotherapy anticancerous drugs or reversing the tumoral cells resistance to vinca alkaloid or antibiotic chemotherapeutic antitumoral drugs or both, which comprises administering to said patient an enhancer agent in an amount effective to sensitive said tumoral cells to vinca alkaloid or antibiotic chemotherapeutic anticancerous drugs or to reversing the tumoral cells resistance to vinca alkaloid or antibiotic chemotherapeutic antitumoral drugs or both; wherein said enhancer agent is a binary vinca alkaloid, analog to vinblastine or vincristine, with a low cytotoxicity or devoid of cytotoxicity and being selected from the group consisting of C-20′ deoxy vincovaline, C-20′-deoxy-deethyl vincovaline, C-16′-epi-C-20′-deoxy-deethyl vinblastine, C-14′-epi-C-20′-deoxy-deethyl vinblastine, C-20′-dimethyl C-20′ deoxy-deethyl vincovaline, C-14′-epi-C-20′-deoxy vinblastine and C-20′-deoxy C-16′, C-20′-epi vinblastine.

3. A method for sensitizing, in a patient in need thereof, tumoral cells to vinca alkaloid or antibiotic chemotherapy anticancerous drugs or reversing the tumoral cells resistance to vinca alkaloid or antibiotic chemotherapeutic antitumoral drugs or both, which comprises administering to said patient an enhancer agent in an amount effective to sensitive said tumoral cells to vinca alkaloid or antibiotic chemotherapeutic anticancerous drugs or to reversing the tumoral cells resistance to vinca alkaloid or antibiotic chemotherapeutic antitumoral drugs or both; wherein said enhancer agent is 20′-deoxy-14′R,20′S,16′R-vinblastine.

4. A method for treating a patient suffering from cancer which comprises administering to said patient an enhancer agent in an amount effective to sensitive tumoral cells to adriamycin or to reverse the tumoral cells' resistance to adriamycin with sequential or simultaneous administration of adriamycin in an effective amount to treat said cancer; wherein said enhancer agent is 20′-deoxy-14′R,20′S, 16′R-vinblastine.

5. A kit of parts for simultaneous separate or sequential use in adriamycin chemotherapeutic anticancerous therapy comprising an effective amount of an enhancer agent and an effective treatment amount of adriamycin, wherein said enhancer agent is 20′-deoxy-14′R,20′S,16′R-vinblastine.

* * * * *